United States Patent
Wyzgala et al.

(10) Patent No.: US 7,252,674 B2
(45) Date of Patent: *Aug. 7, 2007

(54) EXPANDABLE ABLATION BURR

(75) Inventors: Mark H. Wyzgala, Bellevue, WA (US);
Eric B. Hamilton, Bothell, WA (US);
Tom J. Hiblar, Everett, WA (US);
Lixiao Wang, Long Lake, MN (US);
John J. Chen, Plymouth, MN (US);
Irina Nazarova, Woodbury, MN (US);
Nancy L. Haig, East Bethel, MN (US);
Sheng-Ping Zhong, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/770,336

(22) Filed: Feb. 2, 2004
(Under 37 CFR 1.47)

(65) Prior Publication Data
US 2004/0158270 A1  Aug. 12, 2004

Related U.S. Application Data

(63) Continuation of application No. 09/629,771, filed on Jul. 31, 2000, now Pat. No. 6,685,718, which is a continuation-in-part of application No. 09/178,449, filed on Oct. 23, 1998, now Pat. No. 6,096,054.

(60) Provisional application No. 60/076,963, filed on Mar. 5, 1998.

(51) Int. Cl.
*A61B 17/32* (2006.01)

(52) U.S. Cl. ..................... 606/170; 606/180

(58) Field of Classification Search ............... 606/159, 606/170, 180
See application file for complete search history.

(56) References Cited

U.S. PATENT DOCUMENTS

| 4,465,072 | A | * | 8/1984 | Taheri ................... 606/159 |
| 5,030,201 | A | * | 7/1991 | Palestrant .............. 604/22 |
| 5,308,354 | A | * | 5/1994 | Zacca et al. ........... 606/159 |
| 5,318,576 | A | * | 6/1994 | Plassche et al. ....... 606/159 |
| 5,376,100 | A | * | 12/1994 | Lefebvre ............... 606/180 |
| 5,490,859 | A | * | 2/1996 | Mische et al. ......... 606/159 |
| 5,649,941 | A | * | 7/1997 | Lary ..................... 606/159 |
| 5,681,336 | A | * | 10/1997 | Clement et al. ........ 606/159 |
| 5,766,192 | A | * | 6/1998 | Zacca .................... 606/159 |

(Continued)

*Primary Examiner*—Ralph A. Lewis
(74) *Attorney, Agent, or Firm*—Crompton, Seager & Tufte LLC

(57) ABSTRACT

An atherectomy burr has an operating diameter that is larger than the diameter of a catheter in which the burr is routed. The burr may include an expandable polymeric balloon having a partially abrasive exterior surface. The maximum expansion of the burr is controlled by an expansion mechanism. Various mechanisms are disclosed for controlling the maximum diameter of the burr thus preventing the burr from over expanding. In addition, the present invention includes systems that are pulled proximally to remove portions of a lesion located in a patient's vasculature. The system includes an ablation burr that has abrasive disposed on the proximal end. The burr may create a seal when expanded to block the ablated particulate so that an aspiration system can remove the particulate from the vasculature. Alternatively, the burr system may include a self expanding seal that is deployed out of the aspiration sheath.

10 Claims, 20 Drawing Sheets

U.S. PATENT DOCUMENTS

| | | | |
|---|---|---|---|
| 5,897,566 A * | 4/1999 | Shturman et al. | 606/159 |
| 6,096,054 A * | 8/2000 | Wyzgala et al. | 606/170 |
| 6,416,526 B1 * | 7/2002 | Wyzgala et al. | 606/170 |
| 6,685,718 B1 * | 2/2004 | Wyzgala et al. | 606/170 |

* cited by examiner

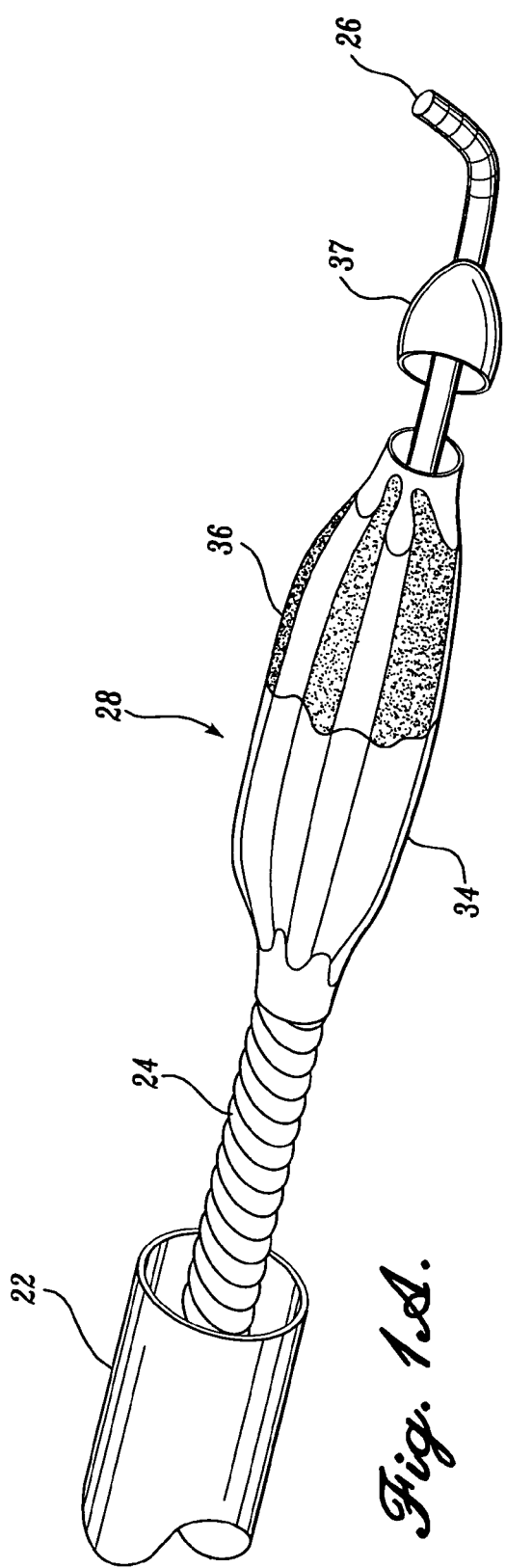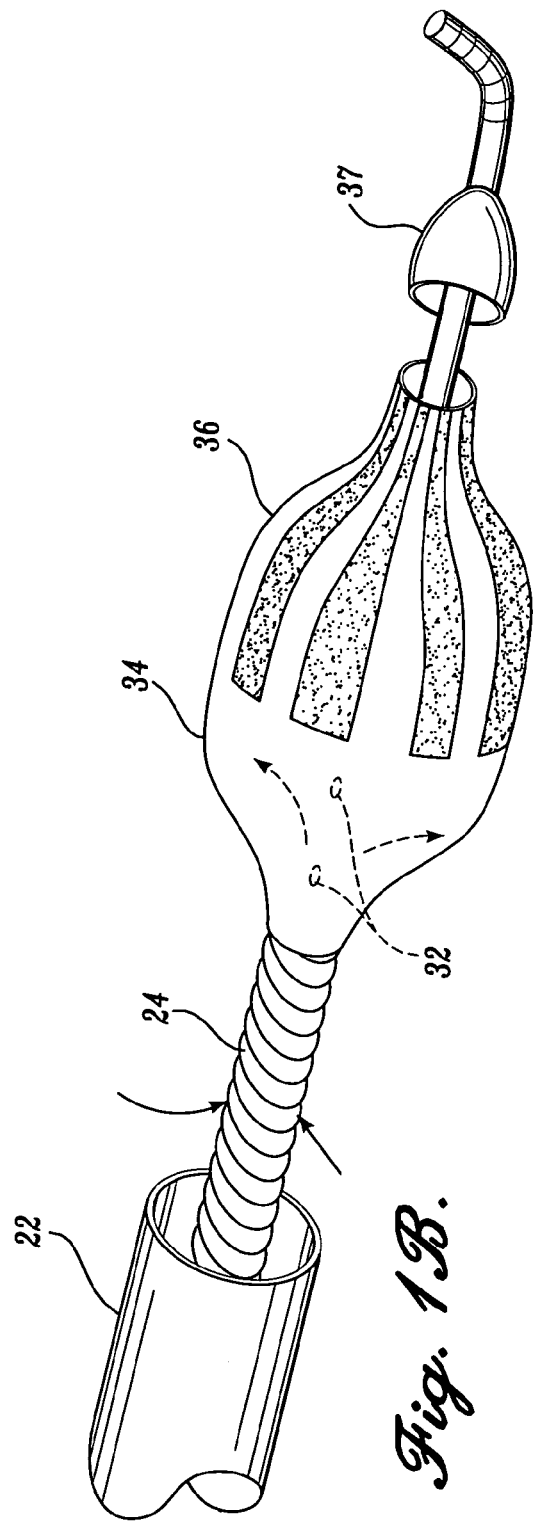

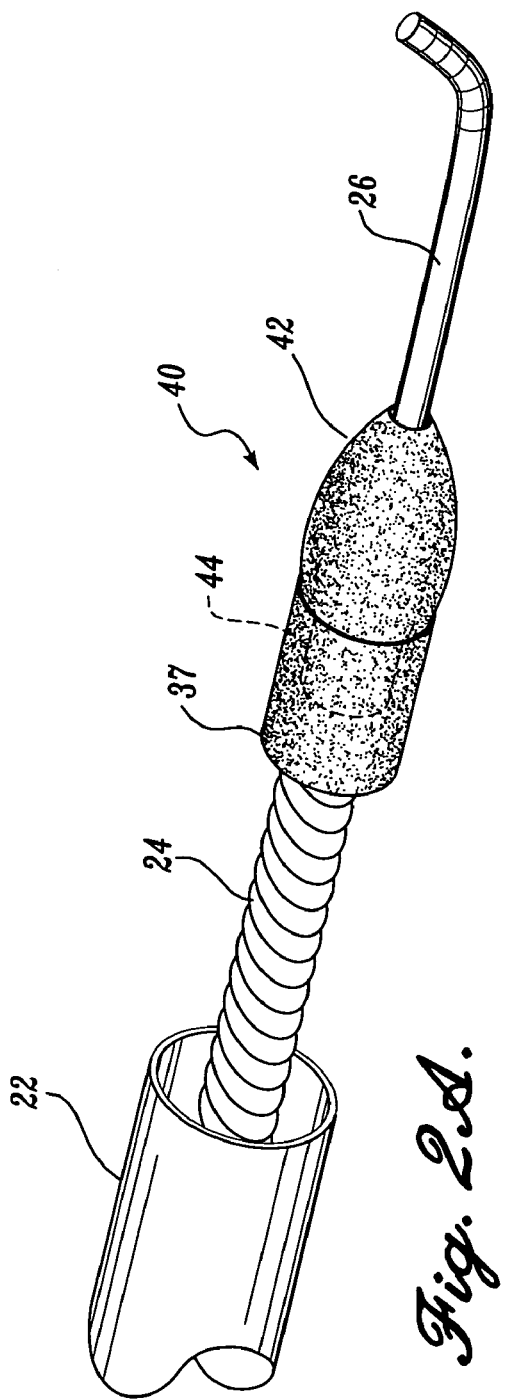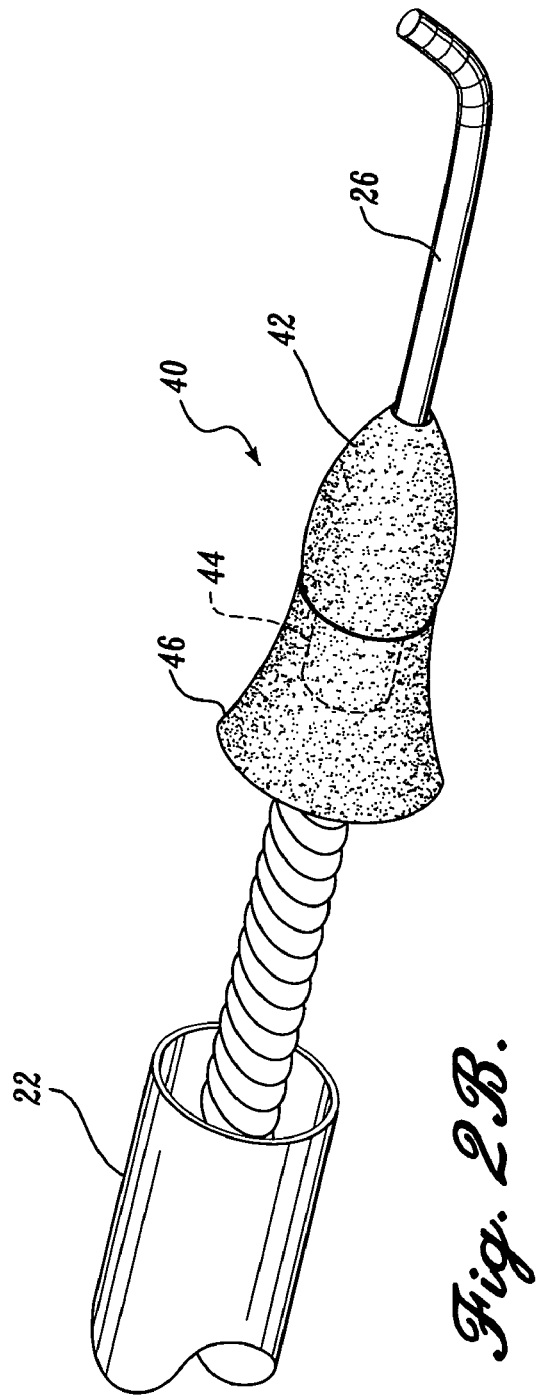

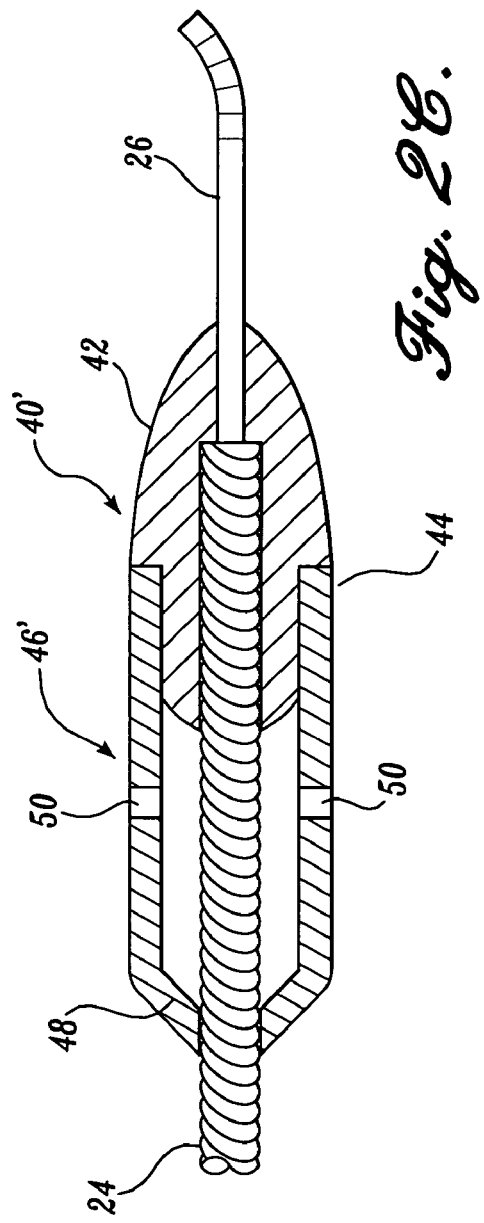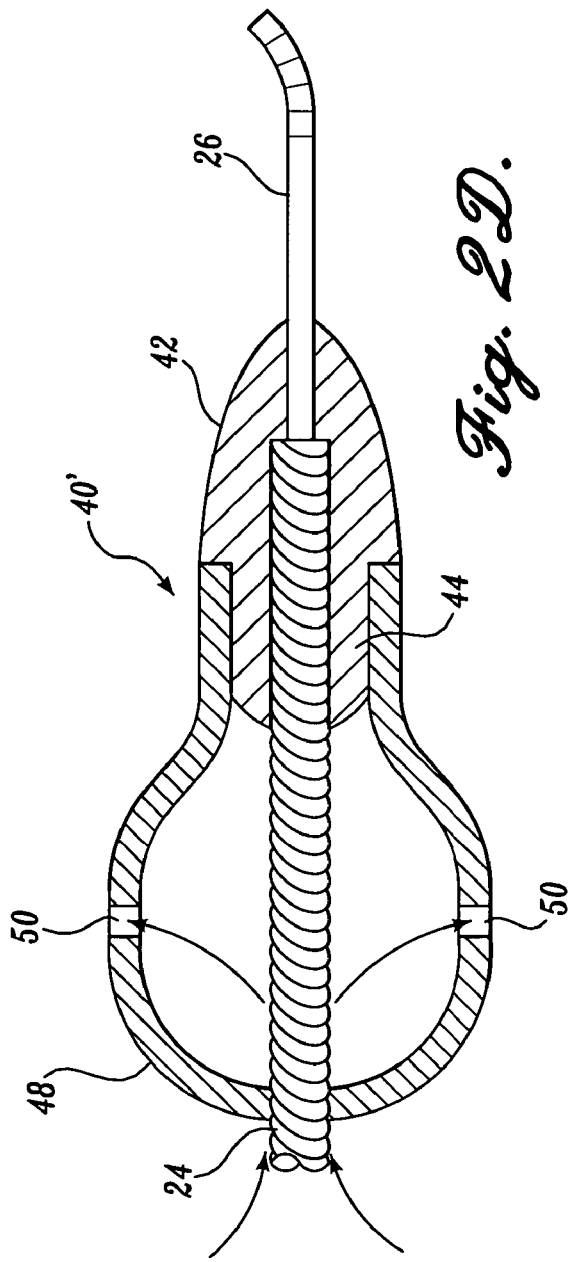

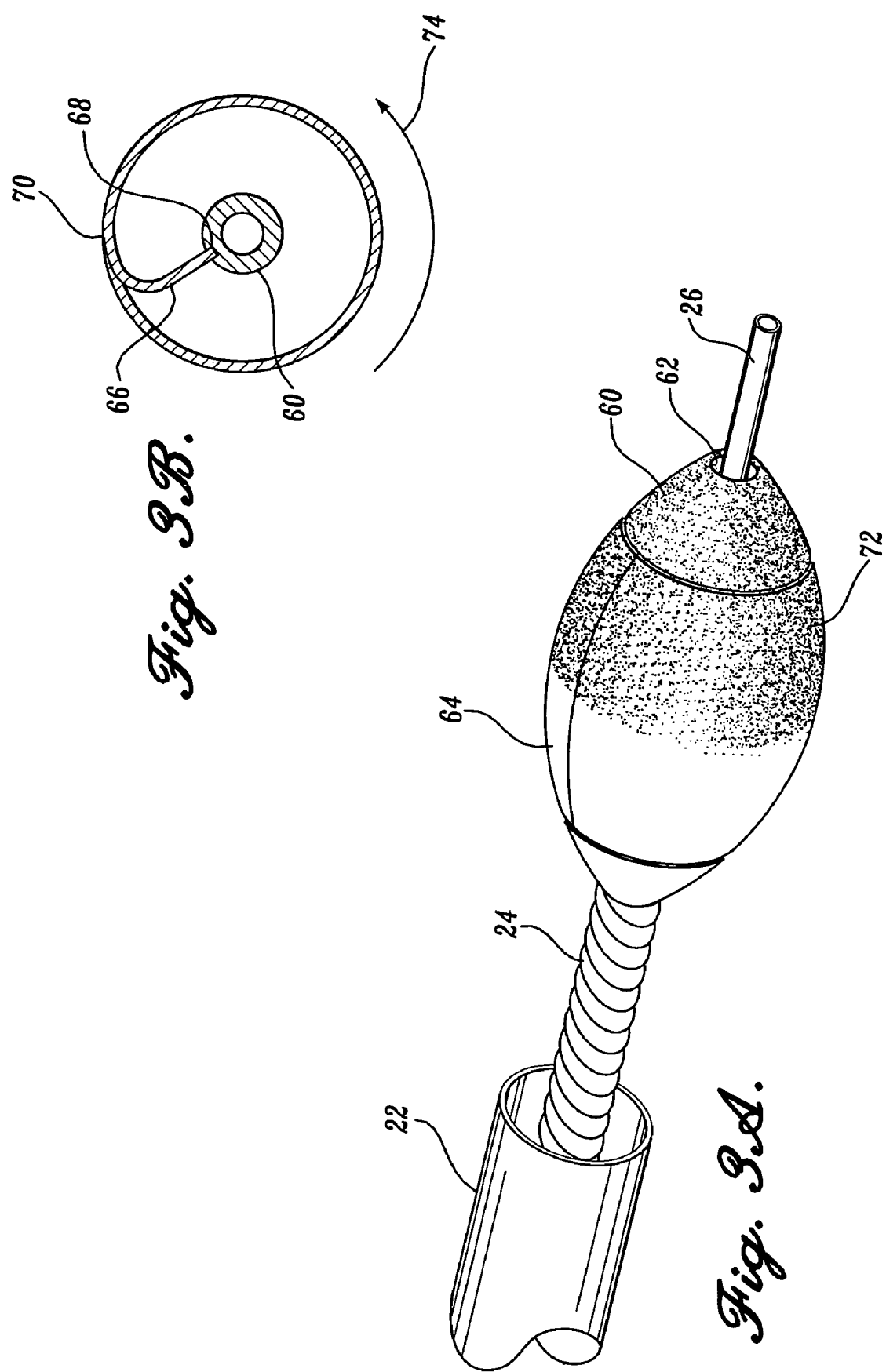

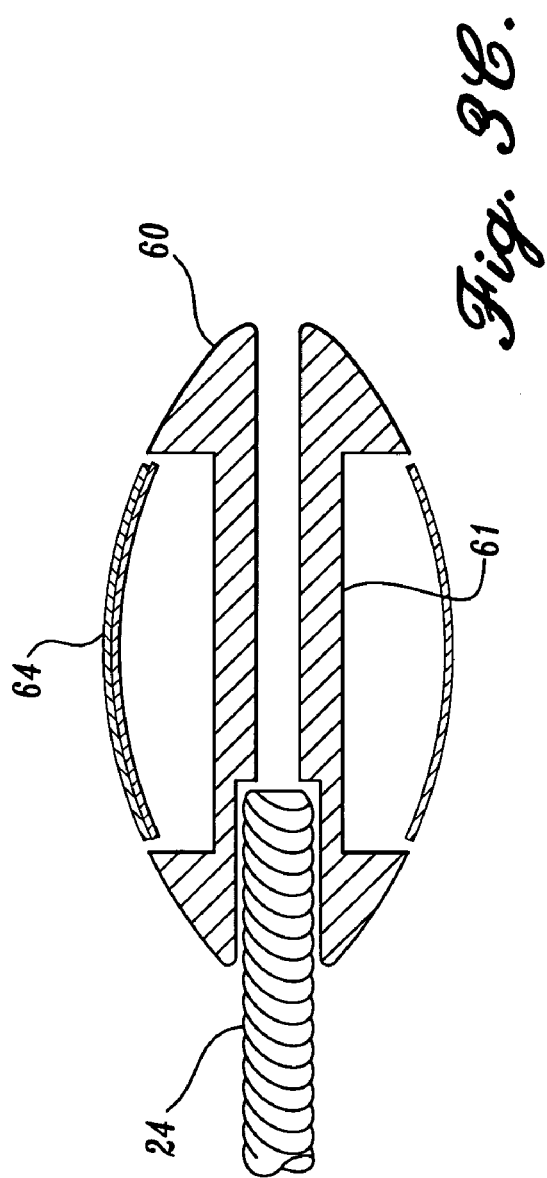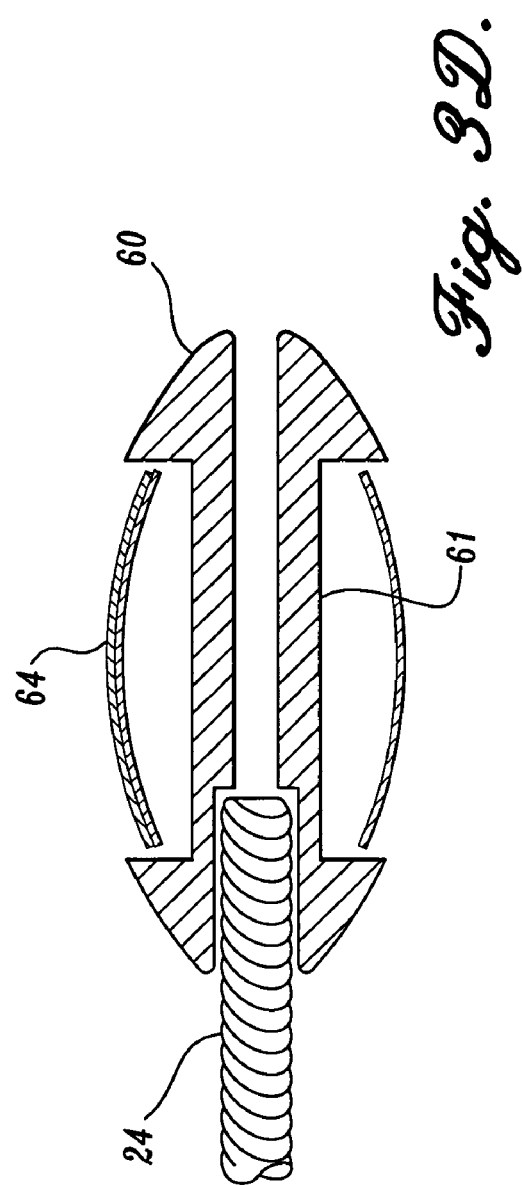

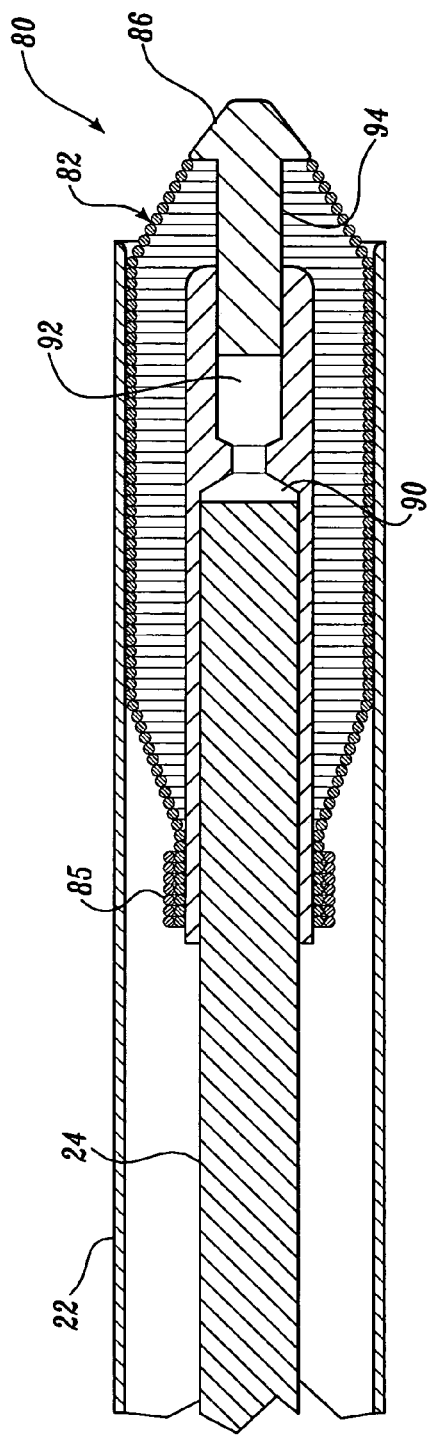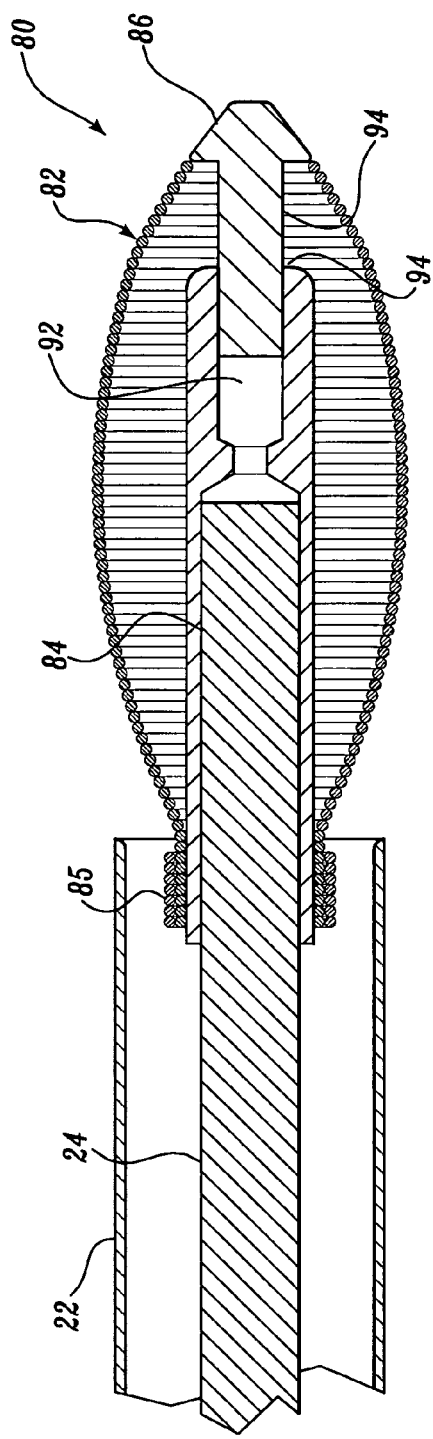
Fig. 4A.
Fig. 4B.

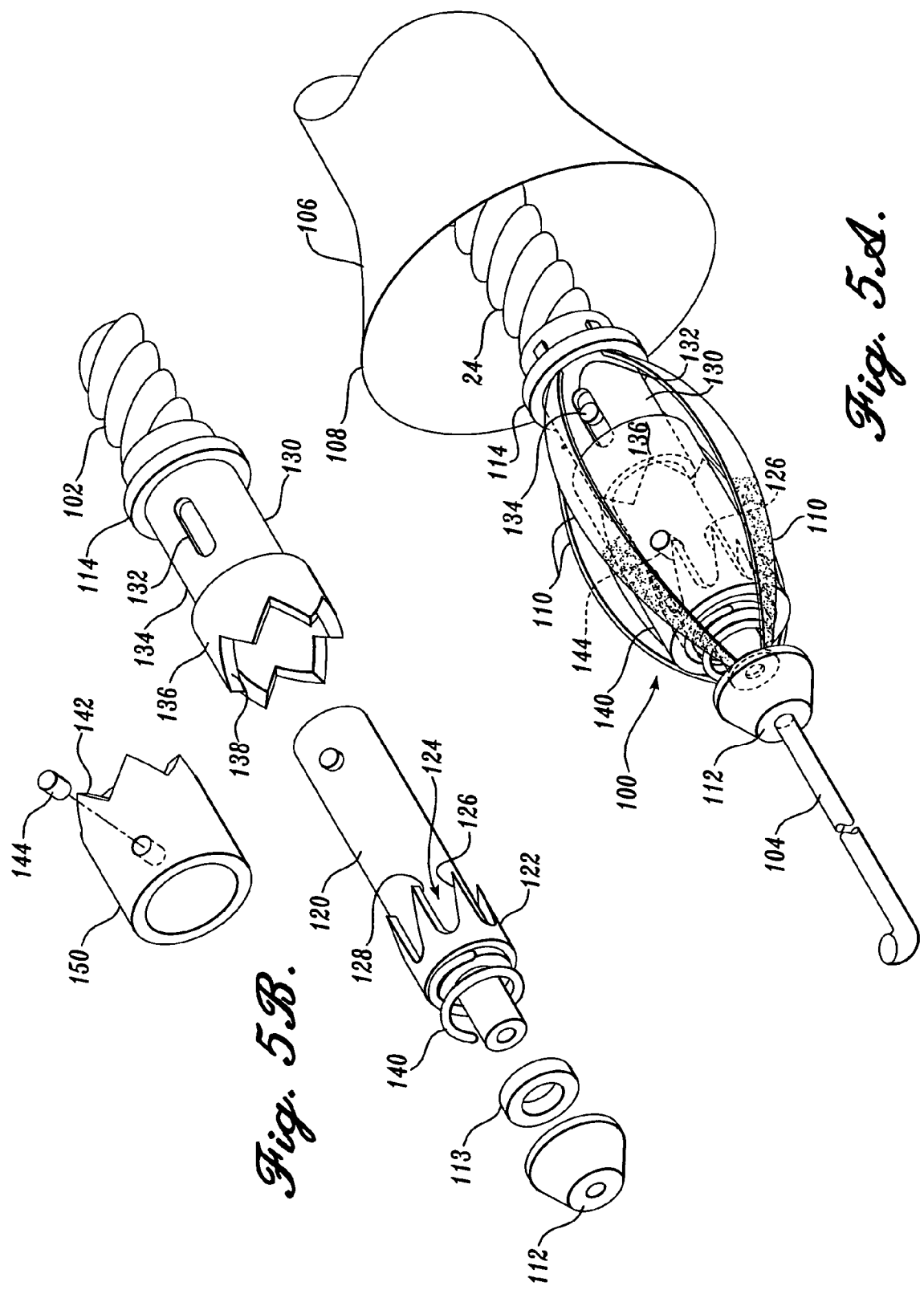

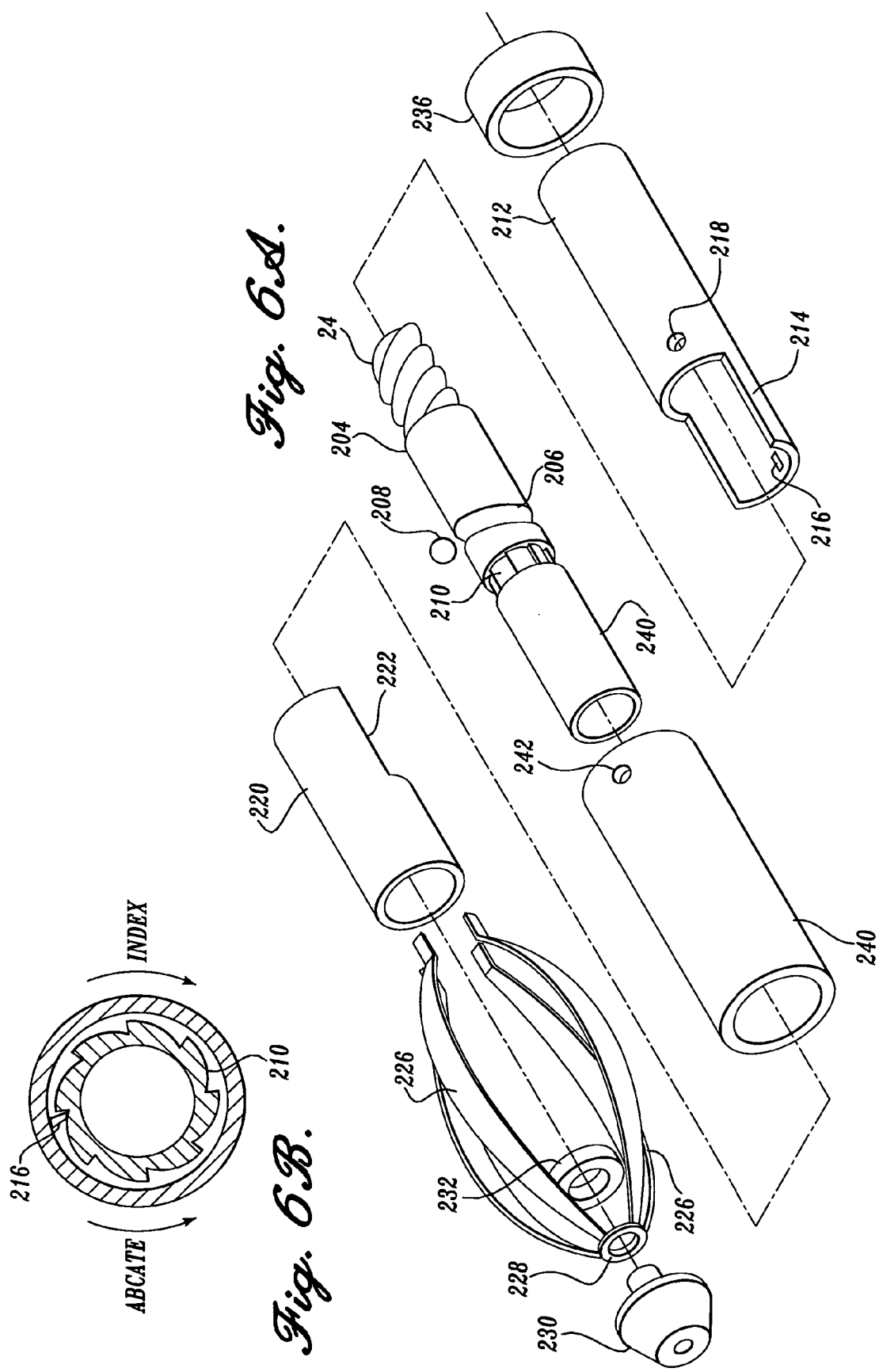

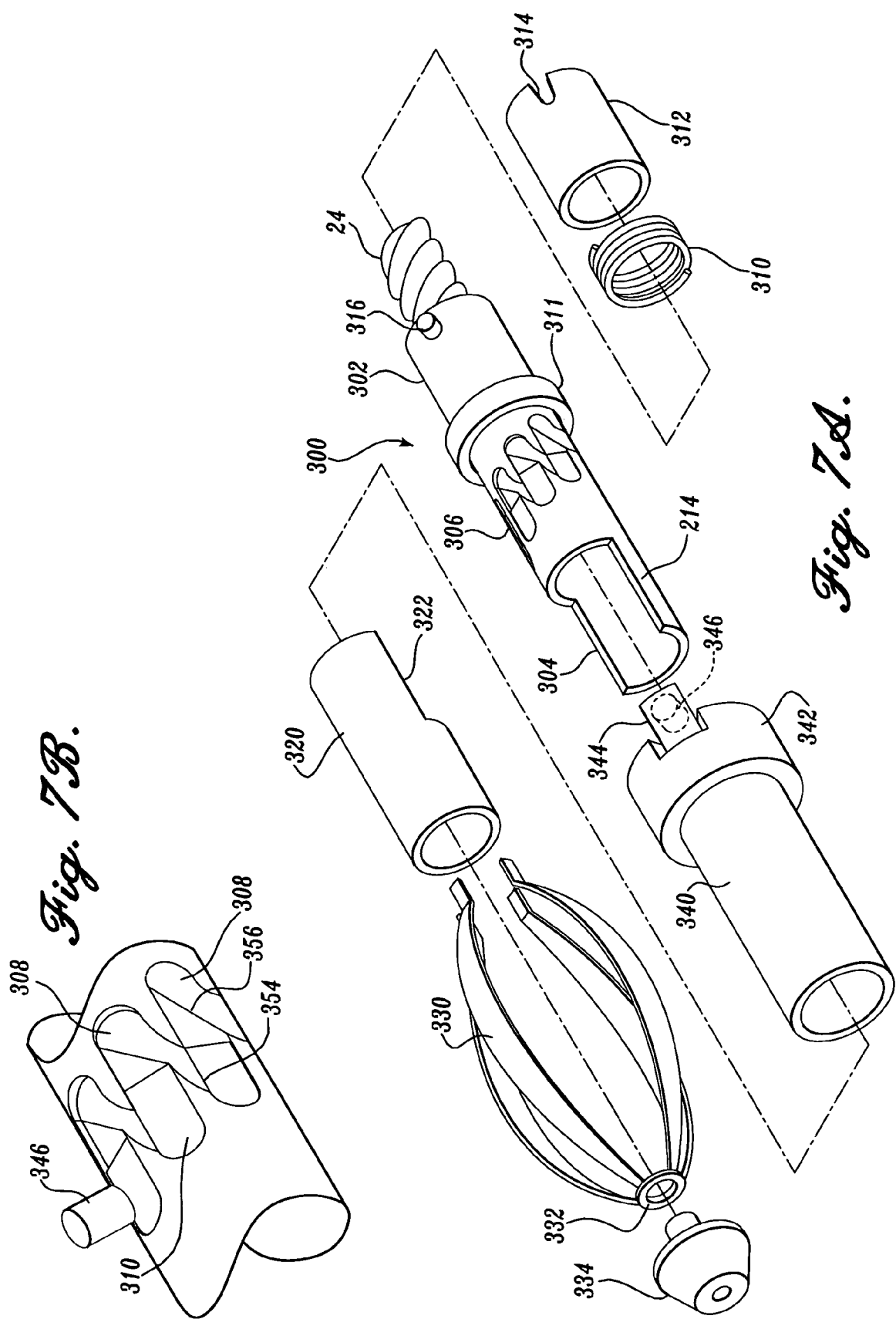

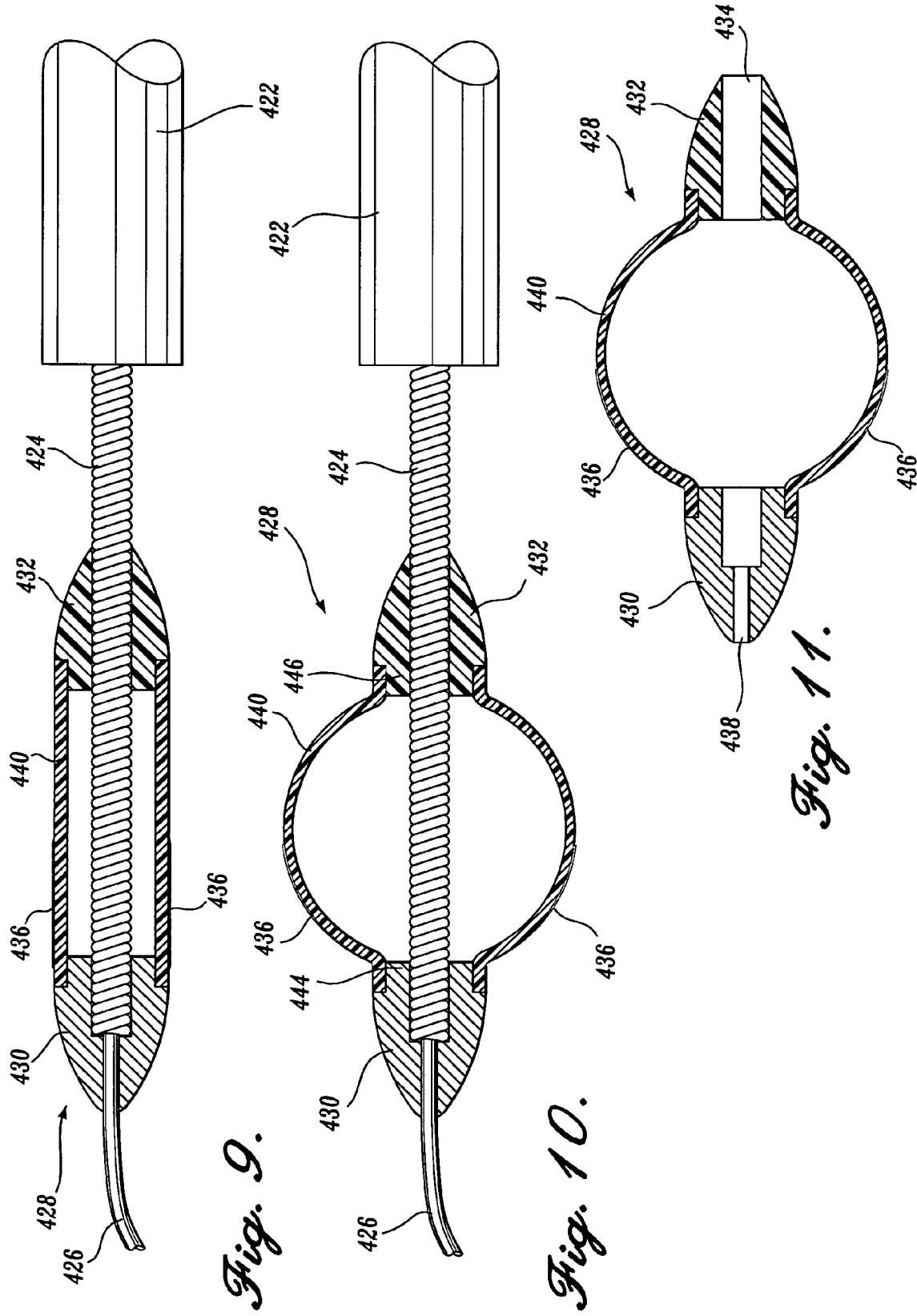

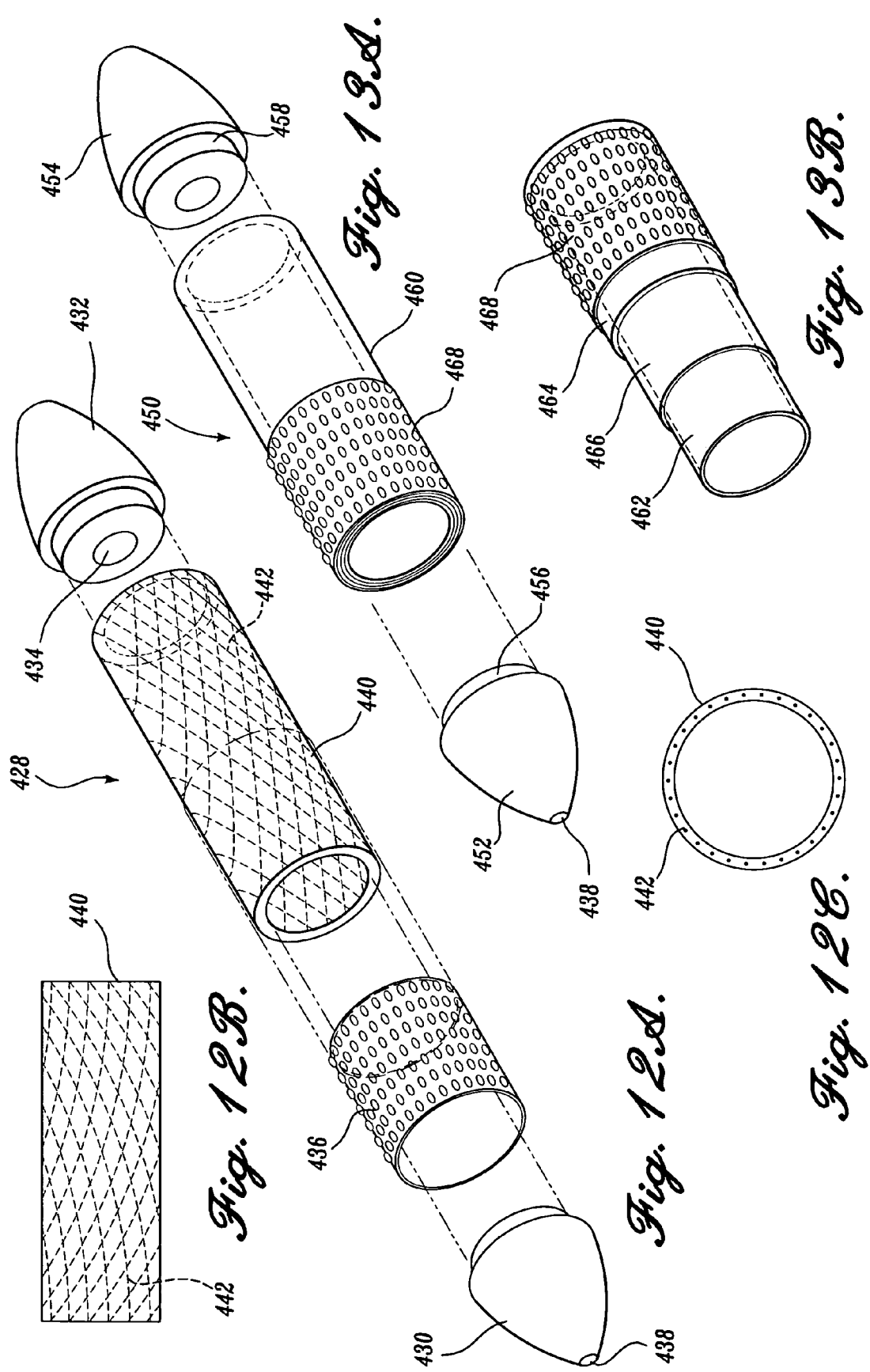

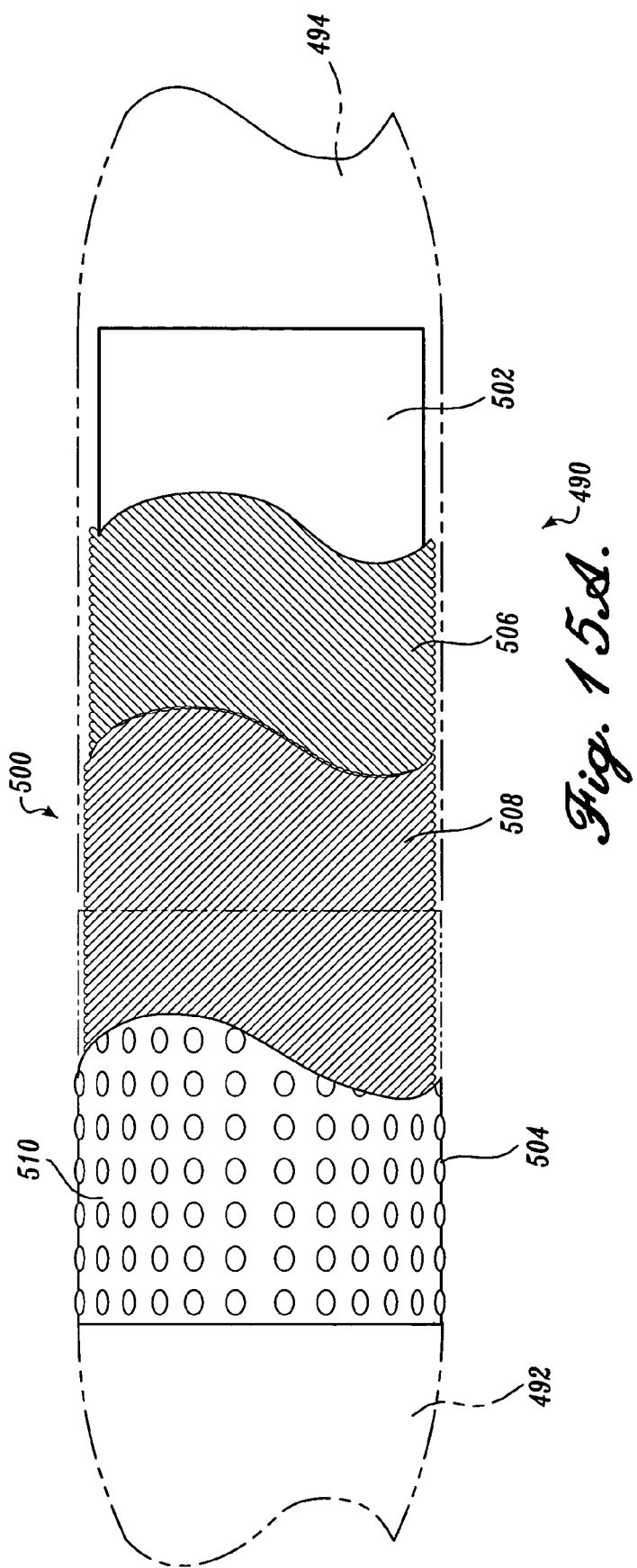
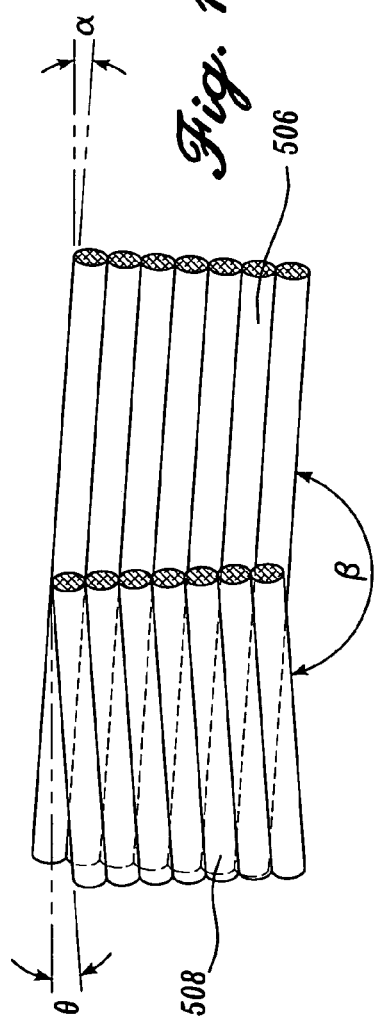
Fig. 15A.
Fig. 15B.

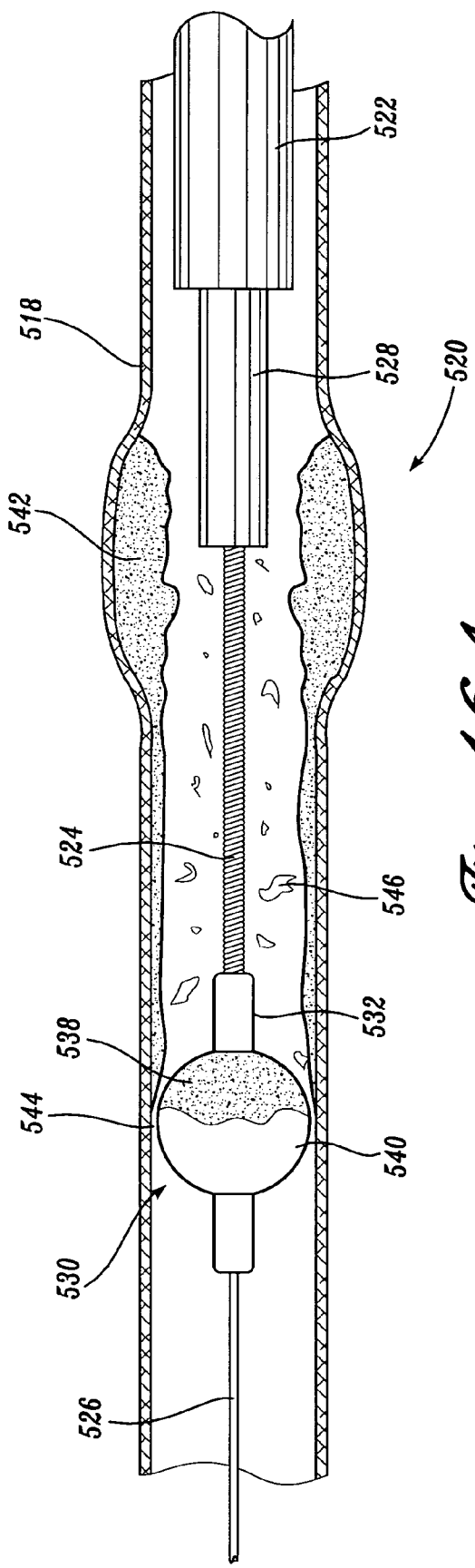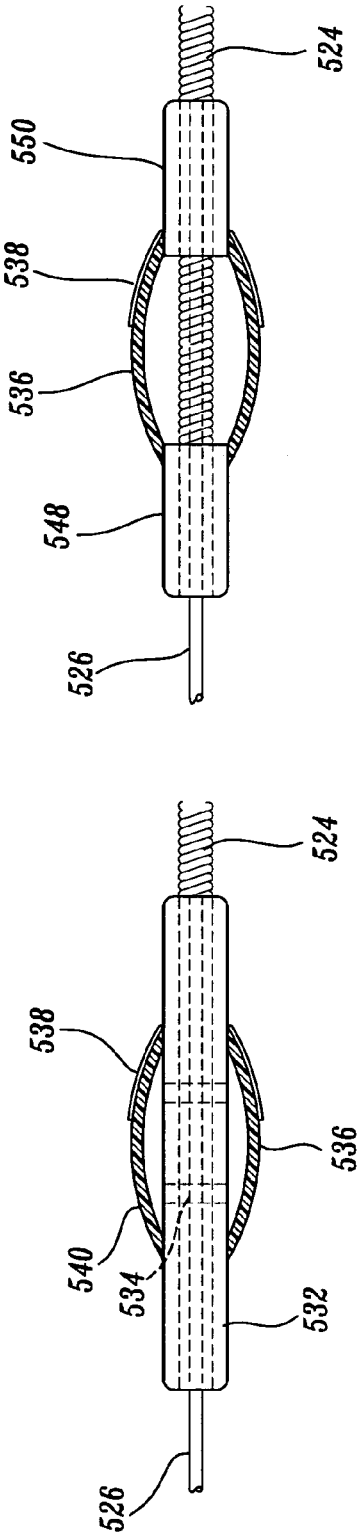

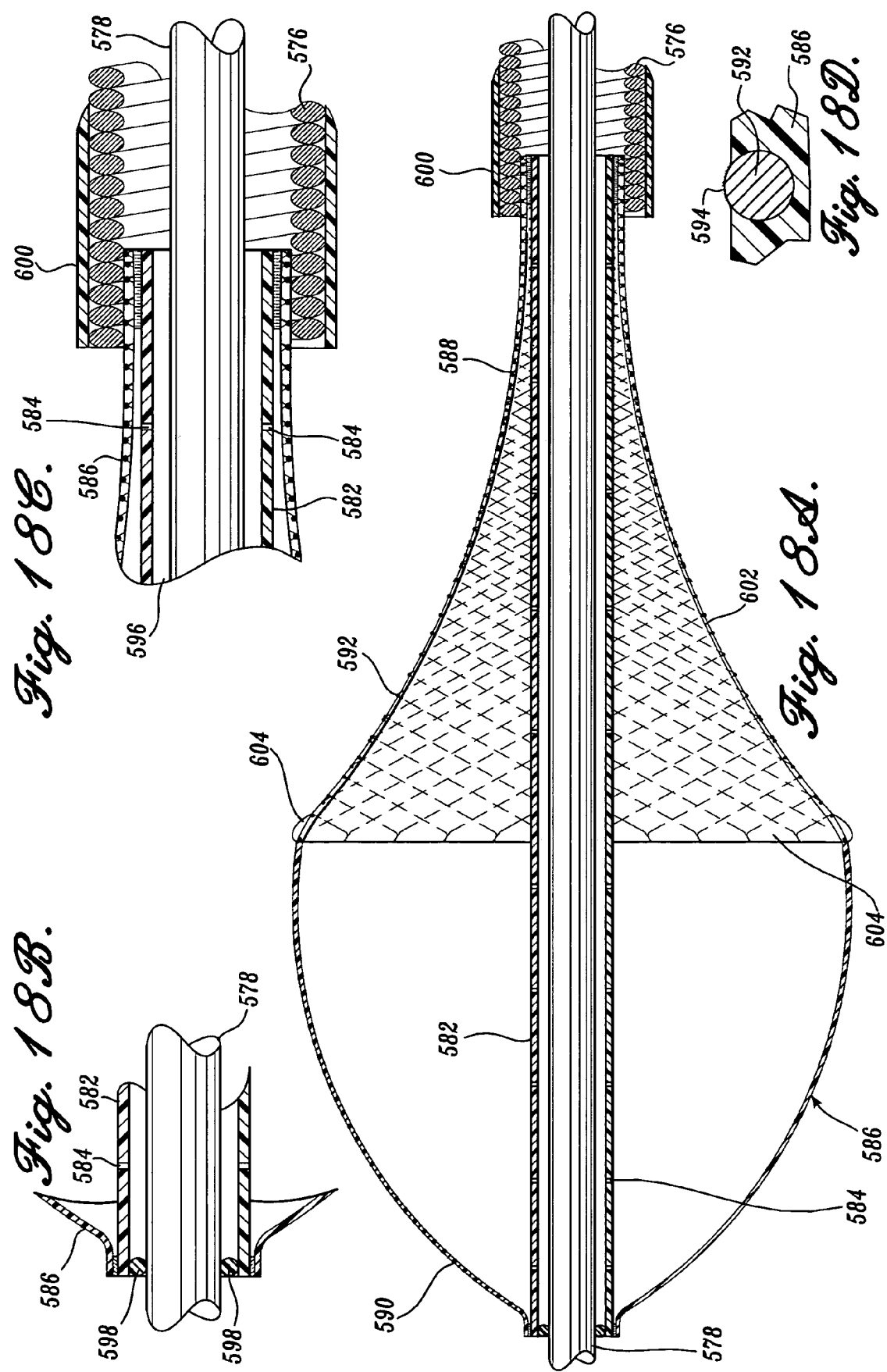

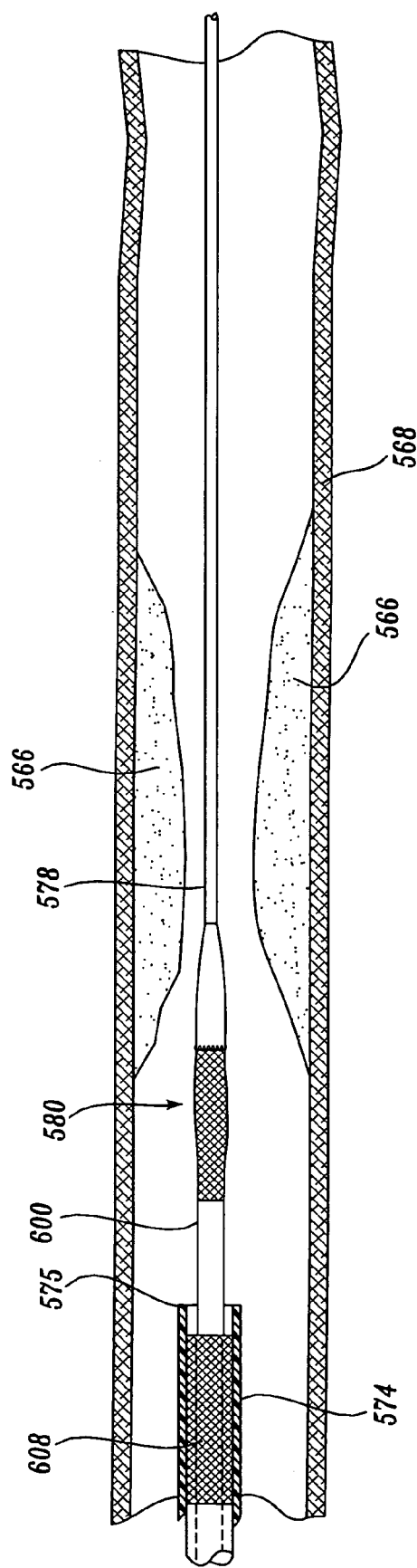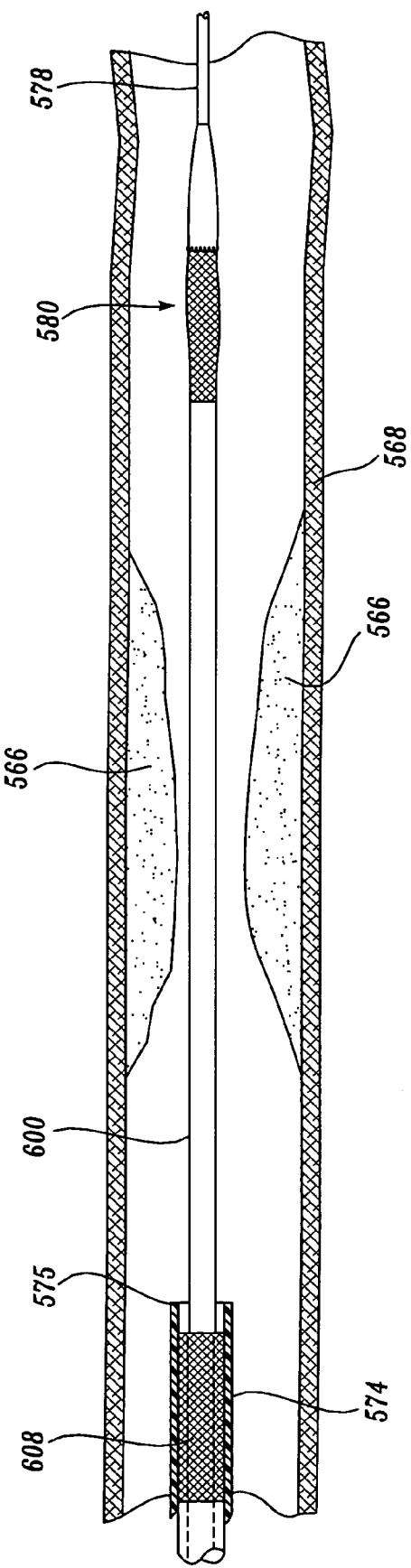

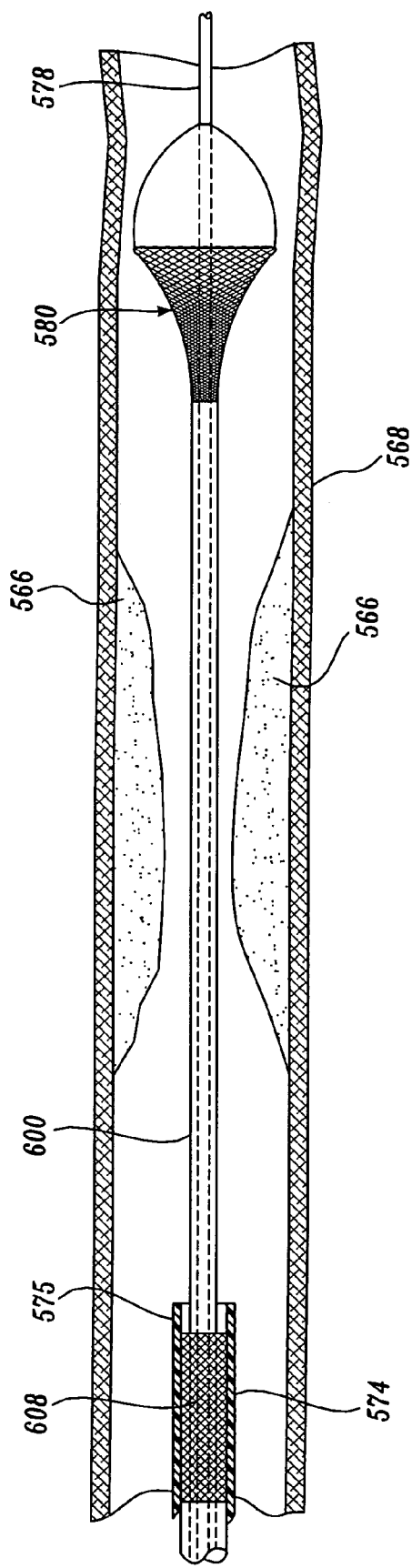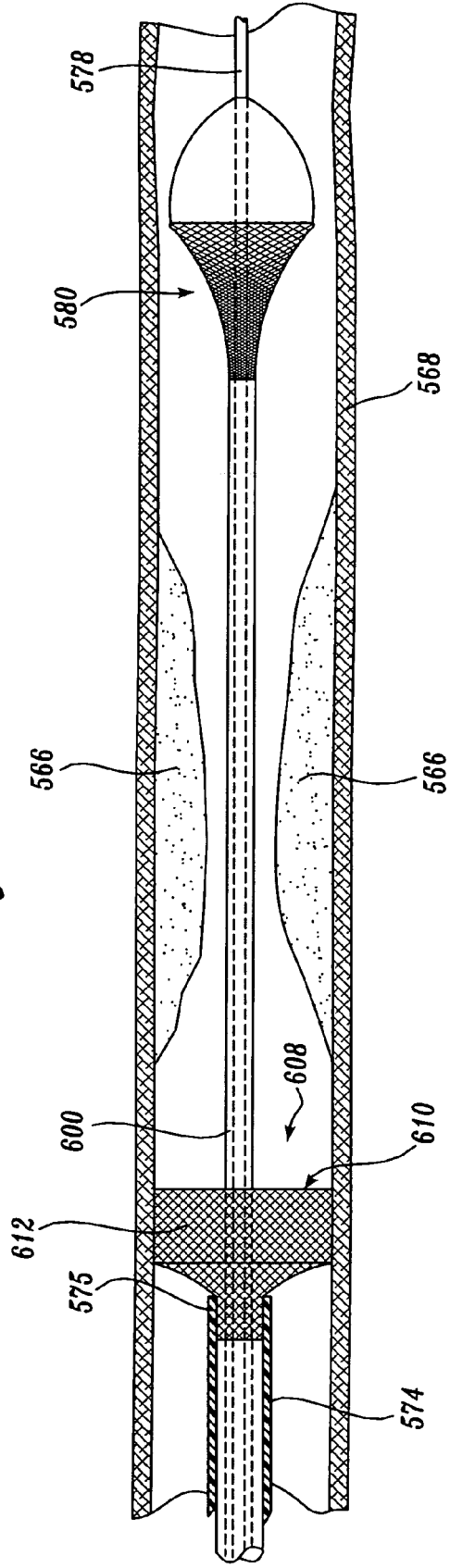

EXPANDABLE ABLATION BURR

CROSS-REFERENCES TO RELATED APPLICATIONS

This application is a continuation of application Ser. No. 09/629,771 filed Jul. 31, 2000, now U.S. Pat. No. 6,685,718, which is a continuation-in-part of application Ser. No. 09/178,449, filed Oct. 23, 1998, now U.S. Pat. No. 6,096,054, which in turn claims benefit from U.S. Provisional Application No. 60/076,963, filed Mar. 5, 1998 all of which are incorporated herein by reference.

FIELD OF THE INVENTION

The present invention relates to medical devices in general, and in particular to atherectomy devices for removing occluding material from a patient's blood vessels.

BACKGROUND OF THE INVENTION

Arteriosclerosis is a common vascular disease in which a patient's blood vessels become hardened and blocked by plaque or clots that impede blood flow. Left untreated, this condition is a major contributing factor to the occurrence of high blood pressure, strokes and cardiac arrest.

To treat arteriosclerosis, many invasive and non-invasive techniques have been developed. For example, cardiac bypass surgery is now a commonly performed procedure whereby an occluded cardiac artery is bypassed with a segment of a healthy blood vessel that is obtained from elsewhere in the body. While this procedure is generally successful, it is fairly traumatic because the entire chest cavity must be opened to access the occluded vessel. Therefore, the procedure is not generally performed on elderly or relatively frail patients.

One example of a promising minimally invasive technique that can be performed on a greater number of patients is to remove the occluding material from a patient's vessel in an atherectomy procedure. To perform this procedure, a guide catheter is typically inserted into the patient's femoral artery and advanced until the distal end of the guide catheter is located in the patient's coronary ostium. A guide wire is then inserted through the guide catheter and traversed into the coronary arteries and past the occluded material to be treated. Then, as described in U.S. Pat. No. 4,990,134, issued to Auth, an atherectomy catheter having a small abrasive burr is advanced through the guide catheter and over the guide wire to the point of the occlusion. The burr is then rotated at high speed and passed through the occlusion to remove particles that are sufficiently small such that they will not occlude in the distal vasculature. As the burr removes the occlusion, a larger lumen is created in the vessel and blood flow is restored.

It is well recognized that the risk of certain patient complications increases with the size of the guide catheter through which minimally invasive devices are routed. Larger guide catheters require larger access holes in the femoral artery, creating the potential for patient complications, such as the sealing of the puncture site after completion of the procedure. Therefore, physicians generally wish to utilize the smallest possible guide catheter during a procedure. However, the smaller size guide catheters can only accommodate corresponding smaller size ablation burrs. Therefore, if a large vessel is to be treated, a larger burr and corresponding larger guide catheter must be used to successfully remove all of the occlusion from the patient's vessel.

In addition, it has also been discovered that when performing an atherectomy procedure as described earlier, it has been beneficial to remove only a small amount of the occlusion at a time. Therefore, currently many procedures are performed using multiple passes through the occlusion with different sized ablation burrs. While these procedures have proven effective, the use of multiple devices for a single procedure adds both time and cost to the procedure.

Given the disadvantages of the existing atherectomy devices, there is a need for an atherectomy device that can treat different size vessels while being traversed through a small guide catheter.

SUMMARY OF THE INVENTION

To eliminate the need for a physician to utilize larger guide catheters in order to route a larger diameter ablation burr in a patient, the present invention comprises an expandable ablation burr. The ablated diameter preferably has a diameter that exceeds the diameter of a guide catheter through which the burr is routed.

According to one embodiment of the invention, the ablation burr includes a polymeric balloon that expands as the burr is rotated. A portion of the balloon is coated with an abrasive such that the balloon will ablate an occlusion as the burr is rotated and advanced through a vessel.

According to another aspect of the present invention, the expandable ablation burr includes an expansion control mechanism which allows the ultimate or final outer diameter of the burr to be predetermined and controlled to create a new lumen in the patient's vessel. The burr includes a nose and end section with an elastic tube section coupled in between. The burr is expanded due to centrifugal force. A portion of the tube section is coated with an abrasive such that the tube section will ablate an occlusion as the burr is rotated and advanced through a vessel.

In one embodiment, the expansion control mechanism includes reinforcement fibers embedded into the elastic tube section. The reinforcement fibers prevent the tube section from over-expanding when rotated. A portion of the tube section is coated with an abrasive such that the expanded tube section will ablate an occlusion as the burr is rotated and advanced through a vessel.

In another embodiment, the tube includes inner and outer layers with the expansion control mechanism containing a layer of ePTFE disposed in-between the inner and outer cast film layers. The ePTFE layer prevents the ablation burr from over-expanding.

In another embodiment, the expansion control mechanism includes post cross-linking of the tube section. The post cross-links prevent the ablation burr from over-expanding.

In yet another embodiment, the expansion control mechanism includes curvilinear ribs on the interior of the tube section. The curvilinear ribs prevent the ablation burr from over-expanding.

In yet another embodiment, the expansion control mechanism includes alternating braided layers of a non-elastic polymeric material in-between the inner and outer layers of the tube section. The alternating braided layers prevents the ablation burr from over-expanding.

According to another aspect of the present invention, a reverse pull-back ablation burr system includes an ablation burr having an abrasive disposed on its proximal end for ablating an occlusion when the burr is pulled back through the occlusion toward the guide catheter. The systems further include an aspiration catheter that aspirates the loose gromous that is ablated by the ablation burr.

In one embodiment, the system prevents the loose gromous of a Saphenous Vein Graft from reembolizing by using the ablation burr in its expanded state as a seal. The burr is pulled back in a reverse fashion to ablate the lesion. Similarly, a distal balloon or filter could be deployed to prevent accident embolization.

In another embodiment, the system prevents the loose gromous from reembolizing by including a self expanding seal coupled to the aspiration catheter. The seal is deployed after the ablation burr is routed through the lesion. As the burr is pulled back in a reverse fashion to ablate the lesion, a vacuum is applied to the aspiration catheter to remove the loose gromous from the vasculature.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIGS. 1A and 1B illustrate an expandable balloon ablation burr according to a first embodiment of the present invention;

FIGS. 2A-2D illustrate an ablation burr with an expandable end according to a second embodiment of the present invention;

FIGS. 3A-3D illustrate an expandable burr that is formed from a strip of superelastic material according to a third embodiment of the present invention;

FIGS. 4A and 4B illustrate an expandable spring ablation burr including an indexing mechanism to control the outer diameter of the burr according to another aspect of the present invention;

FIG. 5A illustrates an isometric view of an ablation burr including an indexing mechanism for selectively changing the outer diameter of the burr according to another aspect of the present invention;

FIG. 5B illustrates the ablation burr shown in FIG. 5A with the parts shown in an exploded relationship;

FIGS. 6A and 6B illustrate another embodiment of an ablation burr with an indexing mechanism for selectively changing the outer diameter of the burr according to the present invention; and FIGS. 7A and 7B illustrate yet another embodiment of an ablation burr with an indexing mechanism for selectively changing the outer diameter of the burr according to the present invention.

FIG. 9 illustrates a cross-sectional view of the expandable ablation burr of FIG. 8 having an expansion control mechanism for predetermining and controlling the maximum outer diameter of the burr according to another aspect of the present invention;

FIG. 10 illustrates a cross-sectional view of the expandable ablation burr of FIG. 9 having a expansion control mechanism for predetermining and controlling the maximum outer diameter of the burr according to another aspect of the present invention in its expanded state;

FIG. 11 illustrates a cross-sectional view of an expandable ablation burr of FIG. 9 having a expansion control mechanism for predetermining and controlling the maximum outer diameter of the burr according to another aspect of the present invention in its expanded state;

FIGS. 12A-12C illustrate an expandable ablation burr including a expansion control mechanism to control the maximum outer diameter of the burr according to another aspect of the present invention;

FIGS. 13A-13B illustrate another embodiment of the expandable ablation burr including a expansion control mechanism to control the maximum outer diameter of the burr according to the present invention;

FIGS. 15A-15B illustrate still yet another embodiment of the expandable ablation burr including a expansion control mechanism to control the maximum outer diameter of the burr according to the present invention;

FIGS. 16A-16C illustrate cross-sectional views of a reverse pull-back expandable ablation burr system according to another aspect of the present invention;

FIGS. 18A-18C illustrate cross-sectional views of the reverse pull-back expandable ablation burr system of FIG. 17A according to the present invention;

FIG. 18D illustrates an expanded view of a cross-sectional view of the balloon in the reverse pull-back expandable ablation burr system of FIG. 17A according to the present invention;

FIG. 19A illustrates a cross-sectional view of the reverse pull-back expandable ablation burr system according to the present invention before the burr has been routed through the lesion;

FIG. 19B illustrates a cross-sectional view of the reverse pull-back expandable ablation burr system according to the present invention after the burr has been routed through the lesion;

FIG. 19C illustrates a cross-sectional view of the reverse pull-back expandable ablation burr system according to the present invention after FIG. 19B when the ablation burr is inflated;

FIG. 19D illustrates a cross-sectional view of the reverse pull-back expandable ablation burr system according to the present invention after FIG. 19C when the self-expanding seal is deployed;

DETAILED DESCRIPTION OF THE PREFERRED EMBODIMENT

Figure 8:
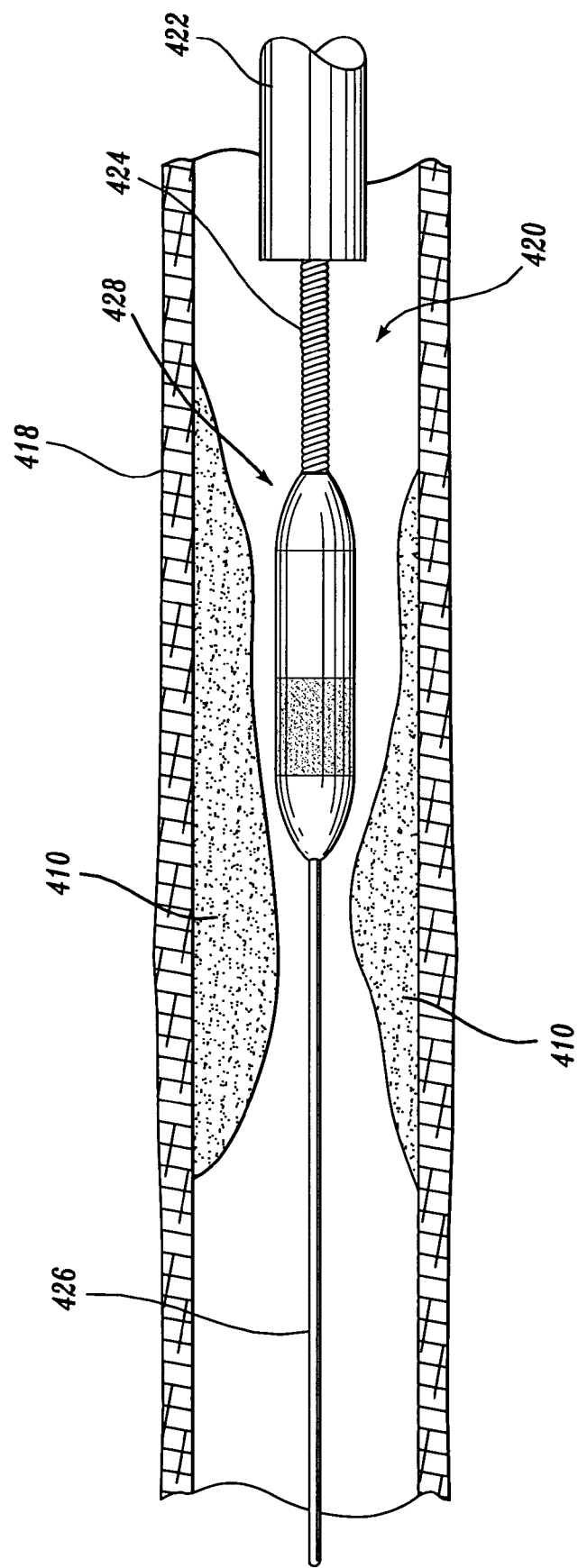
FIG. 8 illustrates an expandable ablation burr including a expansion control mechanism for the predetermining and controlling the maximum outer diameter of the burr according to another aspect of the present invention.

As will be explained in further detail below, the present invention is an ablation burr having an outer diameter that may be expanded to exceed the diameter of a guide catheter through which the burr is routed. Additionally, the present invention is an ablation burr including a mechanism for selectively changing the outer diameter of the ablation burr so that varying sized lumens can be created in a patient's vessel using the same burr. Further, the present invention is an ablation burr including a mechanism for controlling the ultimate or maximum outer diameter of the ablation bur so as to prevent rupturing the burr or damaging the vessel. Finally, the present invention is ablation system including a reverse pull-back ablation burr and an aspiration sheath so as to prevent the ablated particulate from embolizing.

FIG. 1A illustrates an atherectomy device in accordance with a first aspect of the present invention. The atherectomy device 20 is routed from a position outside a patient's body to a point near the site of a vascular occlusion through a guide catheter 22. Extending through the guide catheter 22 is a drive shaft 24 that is coupled at its proximal end to a source of rotational motion such as an electric motor or gas turbine (not shown) that rotates the drive shaft 24 at high speed, e.g., between 20,000 and 250,000 rpm. Disposed at a distal end of the drive shaft 24 is an ablation burr 28 that when rotated by the drive shaft 24 ablates a new lumen through the occlusion in order to permit blood to flow freely through the vessel. Extending through the drive shaft 24 and the ablation burr 28 is a guide wire 26 that can be steered by a physician in order to guide the ablation burr through the vascular occlusion.

As indicated above, it is generally desirable that the ablation burr 28 be routed through the smallest possible guide catheter to the point near the vascular occlusion. In the past, if the diameter of the vessel in which the occlusion was located was greater than the diameter of the ablation burr, the entire atherectomy device including drive shaft, ablation burr and catheter had to be removed from the patient and replaced with a larger diameter catheter that could accommodate a larger diameter burr if all of the occlusion was to be removed. To facilitate maximal lumen size after ablation, the maximum outer diameter of the ablation burr 28 is expandable such that its maximum diameter exceeds the diameter of the guide catheter used to route the burr to the site of the occlusion.

According to the embodiment of the invention as shown in FIGS. 1A and 1B, the ablation burr 28 comprises a length of hypotube 30 coupled to a distal end of the drive shaft 24. The hypotube 30 includes one or more holes 32 that allow fluid to flow in or out of the hypotube. Surrounding the hypotube 30 is a polymeric balloon 34, having an abrasive 36 disposed on at least a portion of the outer surface of the balloon. The distal end of the ablation burr 28 fits behind a concave surface of a tip 37 that prevents the seal of the polymeric balloon from becoming unglued from the hypotube 30 as the burr is advanced through an occlusion.

When the drive shaft is not being rotated, the balloon 34 collapses into an unexpanded state as shown in FIG. 1A. In its unexpanded state, the outer diameter of the ablation burr 28 is smaller than the inner diameter of the guide catheter 22.

When the drive shaft 24 is rotated, fluid surrounding the drive shaft or within the drive shaft is expelled through the holes 32 in the hypotube end into the balloon 34 causing the balloon 34 to expand to its maximum diameter. The maximum diameter is generally larger than the inner diameter of the guide catheter 22. The burr is then advanced through the occlusion to create a lumen in the patient's vessel. When the drive shaft 24 ceases to rotate, the balloon 34 collapses, and the burr can be removed through the guide catheter 22.

In the presently preferred embodiment of the invention, the polymeric balloon 34 is made from a non-stretchable plastic material such as an oriented polyethylene terephthalate polymer (PET). However, it is believed that other plastics or elastomeric materials may also be used.

The abrasive 36 disposed on the outer surface of the balloon preferably comprises small diamond chips approximately 2-60 microns in size.

If the balloon 34 is made of PET, the abrasive 36 is secured to the balloon by creating a thin base layer of silver or gold using vacuum deposition techniques. Once the base layer is applied to the balloon, a layer of metal such as nickel having a slurry of diamond particles disposed therein can be plated to the base layer using an electro- or electroless plating method as is done with conventional burrs.

In some instances, it may be desirable to etch or mask a portion of the base layer with a pattern of dots or other shapes so that the stiff nickel layer does not completely surround the balloon. If the abrasive is only plated to the etched pattern, it may allow the balloon to more easily expand and collapse. In addition to electroplating, it is believed that other techniques could be used to secure the abrasive to the balloon, such as by using an adhesive or chemically bonding sites on the outer surface of the polymeric balloon to which metal ions such as copper, silver, gold, or nickel may bond. These sites may be bonded to the balloon surface using a high-vacuum plasma system or by incorporating chemicals (such as carbon, silver, etc.) with the polymer prior to the extrusion of the balloon. Alternatively, it is believed that pulse cathode arc ion deposition could be used to incorporate bonding sites on the surface of the elastomer.

FIGS. 2A and 2B illustrate another embodiment of an expandable ablation burr according to the present invention. The expandable ablation burr 40 is mounted to the distal end of a conventional drive shaft 24 that rotates the burr at high speeds. A guide wire 26 extends through the drive shaft 24 and the ablation burr 40 so that the burr can guide through a vascular occlusion. The burr is formed as a solid core (except for the lumen through which the guide wire extends) that is made of metal or other suitable material and includes a generally bullet-shaped nose section 42 having a maximum diameter that begins at approximately the midpoint of the burr and tapers in diameter to the distal tip of the burr. The burr 40 also contains a proximal stepped section 44 having a substantially constant diameter that is less than the maximum diameter of the nose section.

Secured over the stepped section 44 of the burr with an adhesive or a mechanical fastener is a polymeric tube 46 having an outer diameter that is substantially equal to or greater than the maximum outer diameter of the nose section 42. The length of the polymeric tube 46 is preferably longer than the length of the stepped section 44 such that a portion of the polymeric tube overhangs the proximal end of the solid core. An abrasive coating is disposed on at least a portion of the outer surface of the tube 46 and the nose section 42. The abrasive is secured to the tube 46 in the same manner as the abrasive is secured to the expandable balloon described above.

When the drive shaft 24 is not rotated, the ablation burr 40 has a maximum outer diameter that is smaller than the inner diameter of a guide catheter 22 through which the burr is routed.

As shown in FIG. 2B, when the drive shaft 24 is rotated, the proximal end of the elastomeric tube 46 expands due to centrifugal force. The proximal end of the ablation burr 40 extends radially outward, therefore allowing the burr to ablate a larger lumen as it is advanced in a vessel. As the drive shaft 24 is slowed, the centrifugal force on the proximal end of the polymeric tube 46 decreases and the outer diameter of the ablation burr returns to its unexpanded state. The ablation burr can then be withdrawn from the patient through the guide catheter 22.

FIGS. 2C and 2D illustrate a cross-section of an alternative embodiment of the expandable ablation burr shown in FIGS. 2A and 2B. An ablation burr 40' includes a generally solid core including a distal nose section 42 and a proximal stepped section 44. A polymeric tube 46' is bonded to the stepped section 44 such that the outer diameter of the polymeric tube is approximately equal to the maximum diameter of the nose section 42 when the burr is in an unexpanded state. In contrast to the embodiment shown in FIGS. 2A and 2B, a proximal end 48 of the polymeric tube 46' is tapered to the drive shaft 24. In addition, the polymeric tube 46' may include one or more holes 50 disposed about its periphery to control the outer diameter of the burr as the burr is rotated.

FIG. 2D illustrates the ablation burr 40' as the drive shaft 24 is rotated. Centrifugal force causes a center section of the polymeric tube that lies between the proximal end of the solid core and the proximal end 48 of the tube to expand radially outward. As the burr begins spinning, centrifugal force expands the polymeric tube. Fluid then fills the interior cavity of the tube and is also acted on by the centrifugal force. To prevent the tube from over expanding, fluid is allowed to vent out the one or more holes 50 that surround the tube 46' such that the volumetric rate at which the fluid vents from the tube reaches an equilibrium with the volumetric rate at which it enters the interior of the tube and the expansion of the tube is halted. The one or more holes 50 increase in size as the speed of the burr increases and the tube expands. As the rotational speed of the ablation burr is decreased, the outer diameter of the burr decreases so that the burr can be withdrawn through the catheter. Because the end 48 of the polymeric tube 46' is closed to meet the drive shaft 24, the polymeric tube 46' is less likely to catch the distal end of the guide catheter as the burr is withdrawn from the patient.

Although the polymeric tube is preferably positioned at the proximal end of the burr, it may be advantageous to place the tube at the distal end of the burr in order to remove certain occlusions.

In simulated ablation tests, the ablation burrs illustrated in FIGS. 2A-2D appear to cause less trauma to the vessel walls and a more even cutting than a conventional burr. In addition, the spinning polymeric tube appears to self center the burr in the center of the patient's vessel. Finally, it is believed that the increased surface area of the polymeric tube creates less heat at the point where it contacts the occlusion, thereby reducing the likelihood of vessel spasm damage or clotting.

It is currently believed that polymer used to make the polymeric tube should have a stress/strain characteristic that allows the materials to be stretched to a known point but not beyond. One technique to achieve the desired stress/strain characteristics is to stretch the polymeric material as it cools. Alternatively, it is possible to incorporate an inelastic string or band into the tube that straightens as the tube expands and reaches a maximum size but cannot be stretched any further.

In some instances, it may be desirable to coat the outer surface of the core and polymeric tube with a hydrophilic coating such as Hydropass™, available from Boston Scientific and described in U.S. Pat. No. 5,702,754, which is incorporated herein by reference. The hydrophilic coating attracts water molecules, thereby making the surface slippery and easier to advance along the guide catheter. In addition, the hydrophilic coating may be beneficial during ablation since less torque may be transferred to a vessel wall if the burr stalls. In addition, the differential cutting ability of the burr may be enhanced due to the increased ability of the burr to slide over soft tissues.

FIGS. 3A-3D illustrate yet another embodiment of an expandable ablation burr according to the present invention. Secured to the distal end of a drive shaft 24 is a mandrel 60. The mandrel is cylindrical and has a generally bullet-shaped nose at the distal and proximal ends and a central lumen 62 extending through it so that the mandrel may be threaded over a guide wire 26. A central portion 61 of the mandrel has a reduced diameter compared to the maximum diameter of the distal and proximal ends. Surrounding the central cylindrical portion 61 of the mandrel 60 is a metallic strip 64 that is coiled around the mandrel as a spring. The metallic strip 64 preferably has a length that is equal to the length between the bullet-shaped ends of the mandrel 60 and a width that is selected such that the strip wraps completely around the mandrel with some overlap onto itself. The metallic strip 64 includes a tab 66 that is fixed within a corresponding slot 68 disposed on the outer surface of the mandrel as shown in the cross-section FIG. 3B viewed from the distal end of the ablation burr. The tab is secured in the slot with either an adhesive or by welding the tab in the slot.

At least a portion of the outer surface of the metallic strip 64 and the distal end of the mandrel 60 is covered with an abrasive 72 that is plated onto the strip and mandrel in order to ablate a vascular occlusion when the ablation burr is rotated.

FIGS. 3C and 3D illustrate a cross section of the drive shaft, metallic strip, and mandrel. In order to fit the ablation burr within the guide catheter 22, the metallic strip 64 is more tightly wrapped around the mandrel in order to reduce its outer diameter as shown in FIG. 3D. Upon emerging from the distal end of the catheter 22, the metallic strip will spring open to resume its original shape shown in FIG. 3C and its outer diameter will therefore increase. Because the proximal and distal ends of the metallic strip 64 are tapered to follow the contour of the bullet-shaped ends of the mandrel, the metallic strip can be recompressed by pulling it into the distal end of the guide catheter 22.

In the presently preferred embodiment of the invention, the metallic strip 64 is made of a superelastic metal such as Nitinol®.

As will be appreciated, to ablate an occlusion in a blood vessel, the metallic strip 64 must be rotated in the direction of the arrow 74 (FIG. 3B) such that an edge 70 of the strip extending along the length of the burr trails the movement of the burr in order to avoid further uncoiling the strip and possibly cutting into the vessel wall.

Yet another alternative embodiment of the expandable ablation burr of the present invention is shown in FIGS. 4A and 4B. The ablation burr 80 includes a coiled wire spring 82 that is wound around the longitudinal axis of a central drive tube 84. Plated to the outer surfaces of at least some of the individual spring coils is an abrasive to ablate an occlusion in a patient's vessel as the burr is rotated. The spring 82 is wound into a generally ellipsoidal shape with a maximum diameter at a midpoint that is larger than the diameter of the guide catheter 22 through which the burr is routed. The distal end of the spring 82 is secured to a nose cone 86 at the distal end of the burr while the proximal end of the spring is secured to the proximal end of the drive tube 84 by a band 85 that overlaps a few proximal coils of the spring.

The drive tube 84 has a proximal lumen 90 into which the distal end of the drive shaft 24 is inserted and secured. A distal lumen 92 of the tube receives a correspondingly shaped shaft 94 that extends from a rear surface of the nose cone 86. The distal lumen 92 and the shaft 94 of the nose cone are shaped such that the shaft moves axially within the lumen but cannot be rotated in the lumen. Therefore, any torque induced in the drive tube 84 by the drive shaft 24 will be transmitted to the nose cone 86 and the distal end of the spring 82. Although not shown in FIGS. 4A and 4B, the drive tube 84 and nose cone 86 preferably include a lumen extending therethrough for passage of a guide wire.

When the ablation burr 80 is positioned in the guide catheter 22 as shown in FIG. 4A, the spring 82 is compressed, thereby reducing its outer diameter. When the ablation burr 80 extends out the distal end of the guide catheter 22, as shown in FIG. 4B, the spring 82 expands into its ellipsoidal shape, thereby increasing the maximum outer diameter of the burr. As the spring 82 expands radially outward, the shaft 94 of the nose cone 86 is drawn into the distal lumen 92. Rotation of the burr will further draw the shaft 94 into the distal lumen 92 until the proximal end of the shaft engages the end of the lumen 92. The length of the lumen 92 and the shaft 94 of the nose cone therefore control the maximum diameter of the spring 82. As a burr is withdrawn into the guide catheter 22, the spring 82 is compressed and the shaft 94 will move distally in the lumen 92.

In many instances, it is desirable to have an ablation burr that can assume several fixed outer diameters. For example, when creating an initial lumen in an occluded vessel, it is generally advisable to utilize the smallest diameter burr available. In the past, if the size of the lumen needed to be increased, the entire ablation burr had to be removed from the patient and successively larger burrs used until a lumen of the desired size was created. To eliminate the need for multiple ablation burrs, another aspect of the invention is an ablation burr with an indexable outer diameter. As the burr is rotated and passed over an occlusion, the outer diameter of the burr can be selectively increased to remove additional occluding material from the vessel.

FIGS. 5A and 5B illustrate a first embodiment of an ablation burr according to the present invention having an indexable outer diameter. The ablation burr 100 is disposed at the distal end of a drive shaft 24. The burr includes a central lumen so that the ablation burr can be passed over a guide wire 104. Surrounding the drive shaft 24 is a catheter 106 having a flared distal end 108 that operates to aid in selectively changing the outer diameter of the burr in a manner described below.

To remove the occluding material from a vessel, the ablation burr includes a number of leaf blades 110 that are secured between a nose cone 112 and a ring 113 at the distal end of the burr. The blades 110 extend proximally over the burr to a leaf retaining ring 114 at the proximal end of the burr. At least a portion of each blade 110 is covered with an abrasive 116 such that when the ablation burr 100 is rotated by the drive shaft 24, the abrasive 116 will remove occluding material from a patient's blood vessel. A polymeric sleeve (not shown) preferably is positioned inside the blades 110 to prevent the blades from causing excessive turbulence in the blood as the burr is rotated.

By selectively changing the distance between the proximal and distal ends of the burr, the amount by which the blades may expand radially outward changes, thereby allowing the burr to create varying sized lumens in a vessel.

As shown in FIG. 5B, to control the diameter of the burr, the ablation burr 100 includes a tube 120 that transmits power from the drive shaft 24 to the distal end of the burr. At the distal end of the tube 120 is an indexing ring 122 having a diameter that is larger than the diameter of the tube 120. In the proximal rim of the indexing ring 122 are a number of slots 124. Each slot includes a first edge 126 that is canted with respect to the longitudinal axis of the tube 120 and a second edge 128 that extends parallel to the longitudinal axis of the tube 120. Each of the slots 124 disposed around the perimeter of the indexing ring has a different depth that controls the outer diameter of the ablation burr.

Pinned to the proximal end of the tube 120 is a drive tube 130. The drive shaft 24 is secured to the proximal end of the drive tube 130. In addition, the drive tube 130 has a central bore through which the tube 120 can fit. The drive tube 130 includes a longitudinally extending slot 132 on its outer surface into which a pin 134 is fitted. The pin 134 is secured to the outer surface of the tube 120 so that the tube 120 can move longitudinally within the drive tube 130 but torque from the drive tube 130 is transferred to the tube 120 or vice versa.

At the distal end of the drive tube 130 is a fixed washer 136. The fixed washer 136 has a diameter that is larger than the diameter of the drive tube 130. The distal rim of the fixed washer 136 includes a number of teeth 138.

Positioned over the indexing ring 122 is a slide washer 140. The slide washer 140 has an inner diameter substantially equal to the outer diameter of the indexing ring 122 and an outer diameter substantially equal to the outer diameter of the fixed washer 136. The proximal rim of the slide washer 140 contains a number of teeth 142 that mate with the teeth 138 of the fixed washer 136. The slide washer 140 also includes a pin 144 that rides along the edges 126 and 128 of the slots 124 in the indexing ring 122. Finally, the burr includes a spring 150 disposed between the back surface of the ring 113 and the distal end of the slide washer 140.

When rotated by the drive shaft 24 or due to the spring of the blades 110, centrifugal force causes the blades 110 to be radially expanded, thereby compressing the tube 120 into the drive tube 130. This in turn causes the pin 144 to slide along a canted edge 126 of a slot 124 in the indexing ring 122. As the pin 144 travels along the canted edge 126, the teeth 142 on the slide washer 140 rotate with respect to the teeth 138 on the fixed washer 136. This "cocks" the teeth of the fixed washer 136 and the slide washer 140 just past their maximum points. The maximum distance by which the drive tube 130 can be compressed over the tube 120 is limited by the depth of the slots 124 extending around the index ring 122, thereby limiting the diameter of the burr.

To index the ablation burr to its next outer diameter, the burr is pulled into the catheter 106. The flared distal end 108 of the catheter engages the blades 110 and compresses them and the spring 150 causes the pin 144 on the slide washer 140 to travel along the straight edge 128 of a slot 124 to a position proximal to the slots of the indexing ring 122. The force of the spring 150 pushes the slide washer 140 proximally thereby causing the teeth 142 on the slide washer and the teeth 138 on the fixed washer to seat and further rotate the pin 144 to the next slot around the indexing ring 122.

In operation, a physician sets the diameter of the burr to the smallest setting to ablate an initial lumen in the patient's vessel. Then, by sequentially spinning the burr, stopping it and retracting it into the catheter, the diameter can be increased or decreased depending on the position of the pin 144 over the indexing ring 122 until a desired lumen diameter is reached.

In the presently preferred embodiment of the invention, the various components of the indexable burr 100 are made by micro-machining. However, it is believed that other fabrication techniques such as metal injection molding or insert molded plastic could also be used.

FIGS. 6A and 6B illustrate another embodiment of an indexable ablation burr according to the present invention. The ablation burr 200 includes a drive tube 204 into which the distal end of the drive shaft 24 is inserted and secured.

The drive tube 204 also includes a race 206 that circumscribes the perimeter of the drive tube. The race 206 is canted with respect to the longitudinal axis of the drive tube such that the race traverses a portion of the length of the drive tube 204. A traveling ball 208 rests within the race 206.

Disposed distal to the race 206 is a series of ratchet teeth 210 that are cut into the outer surface of the drive tube 204. The teeth operate to discretely step the maximum outer diameter of the ablation burr and to transfer the rotational motion of the drive shaft 24 to the burr in conjunction with a rachet tab 216 as described below.

Disposed over the proximal end of the drive tube 204 is a proximal locking tube 212. The proximal locking tube 212 is generally cylindrical but has a stepped section 214 at its distal end such that half the perimeter of the proximal locking tube 212 is removed. The locking tube 212 also includes a ratchet tab 216 that extends inwardly from the inner surface of the locking tube in approximately the middle of the stepped section 214. The ratchet tab 216 engages the ratchet teeth 210 when the proximal locking tube 212 is positioned over the drive tube 204. Finally, the proximal locking tube 212 includes a hole 218 that is cut in the outer surface of the locking tube 212 at a position proximal to the stepped section 214. The hole 218 is sized such that a portion of the traveling ball 208 will extend through the hole 218 when the proximal locking tube 212 is positioned over the drive tube 204.

Axially aligned with the distal end of the drive tube 204 is a distal locking tube 220. The locking tube 220 is generally cylindrical but has a stepped section 222 at its proximal end that mates with the stepped section 214 of the proximal locking tube 212 when the proximal and distal locking tubes are axially aligned. The stepped sections 214 and 222 maintain a rotational coupling between the distal and proximal ends of the ablation burr while allowing the distance between the proximal and distal locking tubes to vary.

Surrounding the burr are a number of blades 226 that extend radially outward from a ring 228. The ring 228 is held in place between a nose cone 230 and a locking ring 232 at the distal end of the burr. The locking ring is secured to the distal end of the distal locking tube 220. The blades 226 are folded back over the outside of the burr and are secured around the proximal end of the locking tube 212 by a leaf retaining ring 236. Although not shown, the ablation burr 200 preferably includes a polymeric liner inside the blades 226 to prevent the blades from causing excessive turbulence in the patient's blood as the burr is rotated.

Finally, the ablation burr 200 includes a traveling tube 240 that fits over the proximal and distal locking tubes 212 and 220. The traveling tube 240 includes a hole 242 disposed in its perimeter. The hole forms a detent into which a top portion of the traveling ball 208 is seated. The distal rim of the traveling tube 240 engages the rear or the proximal surface of the ring 228 from which the blades 226 extend.

To expand or contract the ablation burr 200, the drive shaft 24 is rotated in a direction that is opposite to the direction used during ablation while the blades 226 are held stationary. The ablation burr 200 is retracted into a catheter having a distal end that captures the blades and holds them still as the drive shaft is rotated.

As shown in FIG. 6B, when the drive tube 204 is rotated in the clockwise direction, the ratchet tab 216 rides over the ratchet teeth 210. This causes the traveling ball 208 to move in the race 206 that extends around the outer surface of the drive tube 204 thereby pushing the traveling tube 240 proximally or distally with respect to the drive tube 204.

Because the distal rim of the traveling tube 204 engages the rear or proximal surface of the ring 228 from which the blades 226 extend, the distance between the proximal and distal ends of the blades is varied and hence the maximum expansion of the ablation burr is controlled.

When the drive tube 204 is rotated in the counterclockwise direction and the blades 226 are free, the ratchet teeth 210 engage the ratchet tab 216 causing the traveling tube to rotate with the burr and leaving the traveling ball 208 in the same place in the race 206. Centrifigal force on the blades 226 will cause the nose cone 230 to be drawn proximally until the rear surface of the ring 228 engages the distal rim of the traveling tube 240 and the expansion of the burr is halted. Therefore, by changing the position of the traveling tube 240 over the main tube 204, the maximum diameter of the burr is controlled.

In operation, the physician may position the traveling ball in the race such that the burr has a minimum diameter in order to create an initial lumen in a vessel. Then the burr is then withdrawn into the catheter to hold the blades and the position of the traveling ball changed to increase the size of the lumen without having to remove the atherectomy device from the patient.

Again, parts of the ablation burr 200 are preferably made by machining but could be made by other techniques such as metal injection molding.

FIGS. 7A and 7B show another alternative embodiment of an indexable ablation burr according to the present invention. The ablation burr 300 includes a drive tube 302 into which the distal end of the drive shaft 24 is inserted. The drive shaft 24 extends through drive tube 302 and is secured to a locking tube 320. The drive tube 302 is generally cylindrical except for a stepped semi-circular section 304 at the distal end of the tube, whereby half the circumference of the tube is removed. The drive tube 302 also includes a serpentine channel 306 disposed about the outer surface of the tube proximal to the stepped section 304. The serpentine channel 306 operates to control the maximum diameter of the ablation burr in a manner described below.

Disposed over a proximal end of the drive tube 302 is a spring 310. The spring abuts a ring 311 that is formed around the perimeter of the drive tube 302 to prevent the spring from moving forward on the drive tube. Also disposed over the proximal end of the drive tube 302 behind the spring 310 is a proximal locking tube 312. At its proximal rim, the proximal locking tube 312 includes a notch 314 into which a pin 316 that extends radially outward from the proximal end of the drive tube 302 is inserted. The pin 316 operates to transfer rotation energy of the drive tube 302 to the proximal locking tube 312 while allowing the locking tube 312 some axial motion along the drive tube.

Positioned distal to and axially aligned with the drive tube 302 is a distal locking tube 320. The distal locking tube 320 is generally circular with a stepped semi-circular section 322 that mates with the stepped section 304 on the drive tube 302. At the distal end of the burr are a set of blades 330 that extend outwardly from a ring 332 and are held in place at the distal end of the burr by a nose cone 334 and a retaining ring (not shown). The retaining ring is secured within the distal end of the distal locking tube 320. The set of blades 330 are secured at the proximal end of the burr to the outer surface of locking tube 320. As with the indexable burrs described above, an elastomeric liner is preferably positioned inside the blade to prevent excessive turbulence of the blood in a lumen.

Extending over the drive tube 302 and the distal locking tube 320 is a traveling tube 340. At its proximal end, the traveling tube 340 includes a larger diameter flange 342 with a proximally extending tab 344 secured thereto. Extending radially inward from the end of the tab 344 is a follower pin 346.

As shown in FIG. 7B, the tab 344 and follower pin 346 operate as a cam within the serpentine track 306 that is formed around the outer surface of the drive tube 302. The track 306 includes a number of alternating bends 308, 310 that open towards the distal and proximal ends of the drive tube 302, respectively. Each of the bends 308 that open towards the distal end of the drive tube 302 are located at a different position along the length of the drive tube 302.

The depth of the channel 306 varies as the channel proceeds around the drive tube 302. Positioned in the channel near each of the bends 308, 310 is a step 354. At each step, the depth of the channel increases. The depth then decreases in the channel until the next bend where the depth again increases with a step. This pattern continues around the circumference of the drive tube 302.

As the ablation burr 300 is pulled into a catheter having a distal end which prevents the collapse or bending of the blades 330, a pull on the drive coil causes retraction of the drive tube 302. This causes a relative movement of the traveling tube 340 in a distal direction (relative to the drive tube). The follower pin 346 will move to a distal end of the slot in the serpentine channel 306. Releasing the drive coil will allow spring 310 to move the drive tube 302 distal which will result in the traveling tube pin moving into a proximal end of the slot in the serpentine channel 306. As the pin 346 moves back and forth in the channel, it is forced to move in one direction due to a series of ramps in the channel. As the pin 346 moves to the distal end of a slot, it moves over a ramp which prevents it from returning back down that slot. It is forced to return at an angle down to the adjacent slot. Before reaching the bottom of the adjacent slot, it again travels over a ramp, which prevents it from returning up the slot it had just traveled down. The pin is now in an analogous position to the position in which it started. Because the proximal end of each slot is at a slightly different position (along a proximal/distal line on the drive tube), the overall length of the burr is therefore adjusted with each proximal/distal movement of the pin.

In many instances, it is desirable to have an expandable ablation burr that can expand in a controlled manner to an ultimate or maximum outer diameter. As discussed above, the present invention is an expandable atherectomy burr that can treat different size vessels while being traversed through a small guide catheter. However, it is important that the burr does not expand too far. For example, when using an elastic polymeric material for the expansion tube of the burr, over-expansion of the burr may stretch the burr beyond the elastic range resulting in a permanent, non-recoverable deformation of the burr. To eliminate the need for multiple ablation burrs, another aspect of the invention is an expandable ablation burr with a controlled, ultimate or maximum outer diameter. As the burr is rotated and passed over an occlusion, the ablation burr expands to a maximum outer diameter. The expandable ablation burr with a maximum outer diameter removes the occluding material from the vessel, without the possibility of over-expansion resulting in a ruptured burr or dilated vessel.

FIGS. 8-12C illustrate various embodiments of an ablation burr according to the present invention having a controlled expansion with a maximum outer diameter. The atherectomy device 420 is routed from a position outside a patient's body to a point near the site of a vascular occlusion 410 through a guide catheter 422. Extending through the guide catheter 422 is a drive shaft 424 that is coupled at its proximal end to a source of rotational motion such as an electric motor or gas turbine (not shown) that rotates the drive shaft 424 at high speed, e.g., between 20,000 and 250,000 rpm. Disposed at a distal end of the drive shaft 424 is an ablation burr 428 that when rotated by the drive shaft 424 ablates a new lumen through the occlusion in order to permit blood to flow more freely through the vessel. Extending through the drive shaft 424 and the ablation burr 428 is a guide wire 426 that can be steered by a physician in order to guide the ablation burr through the vascular occlusion 410.

As best shown in FIGS. 9-11, the expandable ablation burr 428 comprises a bullet-shaped nose section 430 coupled to the distal end of drive shaft 424 and a similarly shaped proximal end section 432 in sliding engagement over drive shaft 424. A central lumen 434 extends through end section 432 and a portion of nose section 430 to accommodate drive shaft 424. Nose section 430 is preferably made from a metal material such as brass or the like and is bonded to the drive shaft 424 by an adhesive such as epoxy or the like. Nose section 430 has a maximum diameter that begins proximally and tapers in diameter to the distal tip of the burr. Nose section 430 further contains a proximal stepped portion 444 having a diameter that is less than the maximum diameter of the nose section 430. Located at the distal end of nose section 430 and having a smaller diameter than central lumen 434 is guide wire lumen 438. Guide wire lumen 438 extends through the tip of nose section 430 so that the ablation burr may be threaded over guide wire 426.

The proximal end section 432 of ablation burr 428 is preferably made from a polymeric material such as polyurethane or the like and has a maximum diameter that begins distally and tapers in diameter to the proximal tip of the burr. The end section 432 further contains a distal stepped portion 446 having a diameter that is less than the maximum diameter of the end section 432. The proximal end section 432 may bonded to the drive shaft 424 so that end section 432 rotates with the drive shaft to prevent the tube section from twisting. In an embodiment that does not bond the end section 432 to the drive shaft 424, the inner surface of end section 432 includes a rotational lock, which is described in detail below, so that the end section can slide axially along the drive shaft 424 but cannot rotate separately from drive shaft 424. Therefore, any torque induced by the drive shaft 424 will be transmitted to end section 432.

The rotational lock is comprised of a square shaped bore that extends through end section 432 and a drive shaft with a corresponding shape mateable with end section 432 so that the rotational motion of the drive shaft is transferred to the end section 432. A square shaped metal tube could be bonded to the drive shaft 424 or the drive shaft 424 could be crimped or ground to a square to provide the corresponding shape to rotate end section 432. It should be appreciated to one of ordinary skill that other structures may be used to provide the features of the rotational lock such as a pin/slot arrangement.

Attached to the corresponding stepped portions 444, 446 of nose and end sections is tube or sheath section 440, having an abrasive 436 disposed on at least a portion of the outer surface of the tube section. Tube section 440 is made from a stretchable polymeric or elastomeric material. It is desirable for the material to have a hardness in the range of 50 to 80 shore A and a tensile modulus at 50% elongation of approximately 300 psi in order to expand. Such a material with these properties is a polyurethane made by Dow and sold under the name Pellethane 2103, 70A. However, it is believed that other plastics or elastomeric materials with these properties may also be used.

As shown in FIGS. 12A-12C, reinforcement fibers 442 are embedded into tube section 440 to improve strength, control burr shape during expansion, and determine the ultimate or maximum tube section expansion diameter. The reinforcement fibers 442 are preferably made of polyethylene such as Spectra 1000, 50D, produced by AlliedSignal. However, other fibers such as hydrophilic treated nylon or liquid crystal fiber may be used.

The fiber reinforced polymeric tube section 440 is made by first extruding a small diameter tube of polymeric material. The reinforcement fibers are then braided on the outside surface of the small diameter tube by a conventional braiding machine. A second, larger diameter tube of polymeric material is then extruded over the braided small diameter tube. The heat and pressure from the final extrusion creates the unitary tube section 440.

The abrasive 436 disposed on the outer surface of the tube section preferably comprises small diamond chips approximately 2-60 microns in size. Abrasive 436 is secured to the tube using an electro and/or electro-less plating method. This method has been previously described in conjunction with the embodiment of the present invention shown in FIG. 1. Other methods such as high-vacuum or pulse cathode arc ion deposition may also be used as earlier described.

FIG. 10 illustrates the ablation burr 428 as the drive shaft 24 is being rotated. Centrifugal force causes the center section of the tube section 440, that lies between the proximal end of nose section 430 and the distal end of end section 432, to expand radially outward. As the burr begins spinning, centrifugal force initiates expansion of tube section 440. Fluid then fills the interior cavity of the tube section through drive shaft 424, which is also acted on by the centrifugal force. As the rotational speed of the ablation burr continues to increase, the shape of tube section 440 is controlled at least in part by reinforcement fiber 442. The tube reaches its predetermined maximum outer diameter at a set rotational speed. Even if the burr is rotated past this set rotational speed, the tube section is prevented from further expanding due to reinforcement fibers 442 which are embedded in the tube. As the rotational speed of the ablation burr is decreased, the outer diameter of the burr decreases so that the burr can be withdrawn through the guide catheter that surrounds the driveshaft.

It will be appreciated to one of ordinary skill in the art that the dimensions and patterns of the fiber reinforcement is determined by the mechanical requirements of the composite burr and can be used to determine the maximum expansion diameter of the burr so as to avoid rupturing the burr or dilating the vessel. For example, the braid pic count, or the number of cross points of the fiber per inch of length, may vary to allow the tube section to expand to a certain predetermined amount. A pic count in the range of 10-30 has been used with Pellethane 2103 70A to allow for ample expansion but also still possessing the ability to restrict the expansion of the tube to a definite maximum outer diameter. However, different pic count ranges may be used with different polymeric materials.

FIGS. 13A-13B illustrate another embodiment of a maximum outer diameter ablation burr according to the present invention. As shown in FIG. 13A, the expandable ablation burr 450 is mounted to the distal end of a conventional drive shaft (not shown) that rotates the burr at high speeds. Ablation burr 450 includes a tube or sheath section 460 with proximal and distal ends and having an abrasive 468 disposed on at least a portion of the outer surface of the tube.

The distal end of tube section 460 is attached to the reduced diameter stepped portion 456 of the nose section 452 and the proximal end of the tube is attached to the reduced diameter stepped portion 458 of end section 454 in a manner similar to as previously describe in FIG. 9 for ablation burr 428. Tube section 460 contains two layers 462, 464 of a stretchable cast film. An intermediate layer 466 of expanded polytetrafluoroethylene (referred hereinafter as ePTFE) with a pore size of about 1 micron is disposed between the layers of cast film to control the shape and expansion of the burr. This is achieved because ePTFE has a natural characteristic of growing narrower as it is stretched. By holding the width constant between the cast film layers, the ePTFE will have a limited ability to stretch.

The tube section 460 is made by first applying a 5% solution of tetrahydrofuran (THF) and polyurethane to the top and bottom surfaces of the ePTFE layer 466 and allowing the solution to penetrate. Cast film layers 462, 464 are placed on both sides of the ePTFE and wrapped around a mandrel. The wrapped tube is heat set at about 160 degrees Celsius for approximately 30 minutes to fuse the layers together to form unitary tube section 460.

In operation, as previously described in FIG. 9, the ablation burr 450 is rotated by a drive shaft (not shown). Centrifugal force causes a center section of the polymeric tube section 460, that lies between the proximal end of nose section 452 and the distal end of end section 454, to expand radially outward. As the burr begins spinning, centrifugal force initiates expansion of tube section 460. Fluid then fills the interior cavity of the tube through drive shaft 424 and is also acted on by the centrifugal force. As the rotational speed of the ablation burr continues to increase, the shape of tube section is controlled by ePTFE layer 466. The tube reaches its predetermined maximum outer diameter at a set rotational speed. Even if the burr is rotated past this set rotational speed, the tube section is prevented from over expanding due to ePTFE layer 466 which is fused between cast film layers 462, 464 of tube section 460. As the rotational speed of the ablation burr is decreased, the outer diameter of the burr decreases so that the burr can be withdrawn through the catheter.

The abrasive 468 is disposed at the distal end of the outer surface of the tube section 460, and preferably comprises small diamond chips approximately 2-60 microns in size. Abrasive 468 is secured to the tube using an electro or electro-less plating method. This method has been previously described in the embodiment shown in FIG. 1. Other methods such as high-vacuum or pulse cathode arc ion deposition may also be used as earlier described.

In the above-described embodiment, the use of one layer of ePTFE was described. However, it may be desirable to use multiple layers disposed at different angles with respect to each other to control the expansion of the burr. Further, in the above-described preferred present embodiment, the cast film is a polymeric material such as polyurethane. However, other polymeric or elastomeric material may be used.

In another embodiment of the invention, a stretchable material with post-crosslinking capabilities is extruded into a tube or sheath section. The tube section (not shown) having an abrasive disposed on at least a portion of the outer surface of the tube section, is used as the expandable section of the ablation burr. The tube section is crosslinked by exposing the tube to radiation. The tube section may also be crosslinked by a water initiated crosslinking function group during the extrusion quench process. The expansion of the tube can be controlled or adjusted by the crosslinking density.

Abrasive is disposed at the distal end of the outer surface of the tube section, and preferably comprises small diamond chips approximately 2-60 microns in size. The abrasive is secured to the tube section using an electro or electro-less plating method. This method has been previously described in the embodiment shown in FIG. 1. Other methods such as high-vacuum or pulse cathode arc ion deposition may also be used as earlier described. Further, in the preferred present embodiment, the post-crosslinking tube may be a polymeric material such as polyurethane. However, other polymeric or elastomeric material with post-crosslinking capabilities may be used.

FIGS. 14A-D illustrate another embodiment of a maximum outer diameter ablation burr according to the present invention. As shown, an expandable ablation burr 470 is mounted to the distal end of a conventional drive shaft (not shown) that rotates the burr at high speeds. The ablation burr 470 includes a stretchable tube or sheath section 480 with proximal and distal ends. The distal end of the tube section 480 is attached to a reduced diameter the stepped portion 476 of the nose section 472, and the proximal end of the tube section is attached to a reduced diameter stepped portion 478 of end section 474 as previously described with respect to FIG. 9.

Figure 14A:
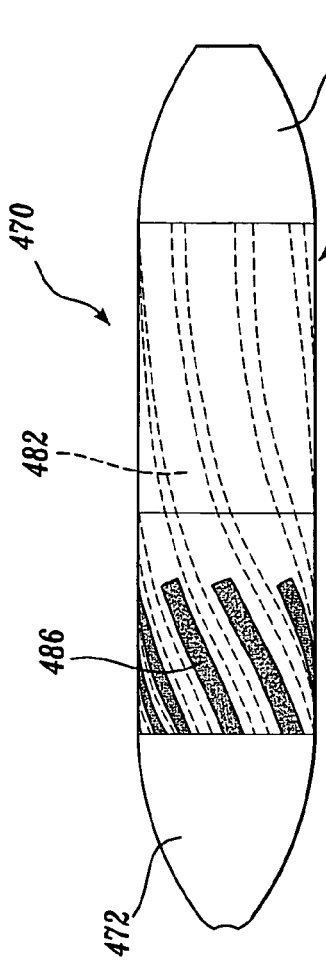
FIGS. 14A-14D illustrate yet another embodiment of the expandable ablation burr including a expansion control mechanism to control the maximum outer diameter of the burr according to the present invention.
Figure 14B:
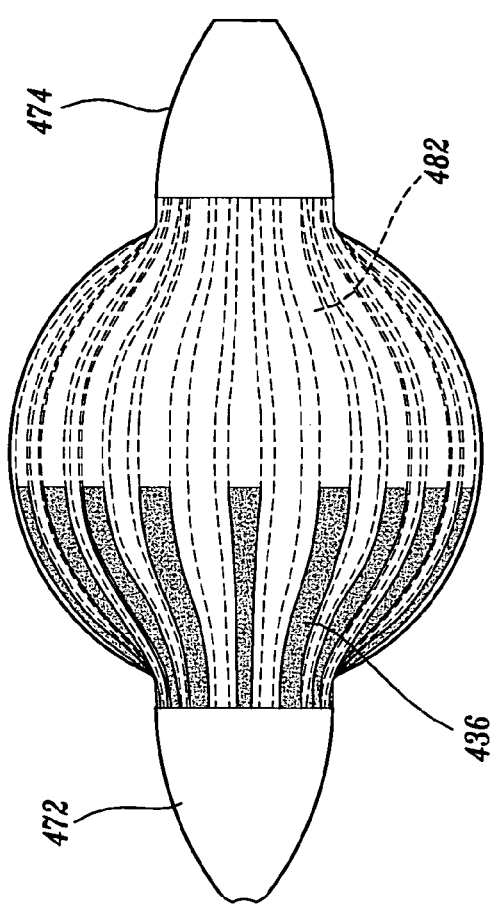
Figure 14C:
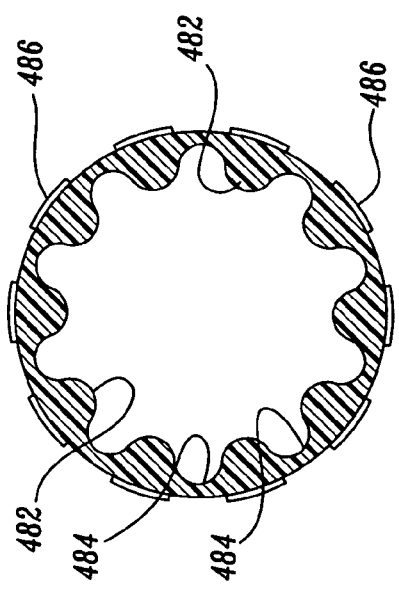
Figure 14D:
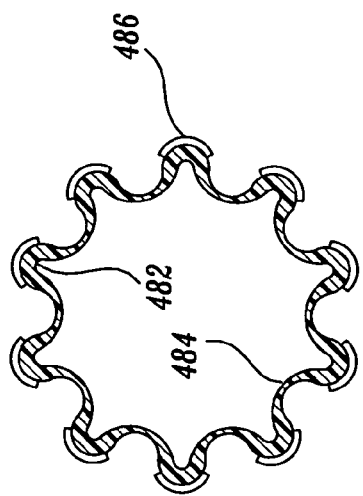

As shown in FIGS. 14A and 14C, tube section 480 in an unexpanded state includes curvilinear ribs 482 extending longitudinally from nose section 472. Curvilinear ribs 482 are nominally spiraled along the length of the burr 470. As shown in FIG. 14C, curvilinear ribs 482 are formed as relatively thick internal ridges extending radially inward from the outer surface of tube section 480. Curvilinear ribs 482 alternate between channel-like sections 484 on the inner surface of the tube section. Channel-like sections 484 also extend radially inward. However, as compared to curvilinear ribs 482, channel-like sections 484 do not extend inward as far so as to create a tube section having a wall with alternating thickness.

The abrasive 486 is disposed on the outer surface of the tube section directly above internal ribs 482, and preferably comprises small diamond chips approximately 2-60 microns in size. By disposing the abrasive directly over the internal ribs on the outer surface of the tube section, the shear force between the abrasive 486 and the tube section 480 is reduced when section 480 expands (shown in FIG. 14B), allowing the abrasive to adhere to the tube section better than a uniform elastomer Abrasive 486 is secured to the tube using an electro or electro-less plating method as described above. Other methods, such as high-vacuum or pulse cathode arc ion deposition, may also be used as earlier described.

FIG. 14B illustrates the ablation burr 470 as the drive shaft 424 is rotated. Centrifugal force causes the tube section 480 that lies between the proximal end of nose section 472 and the distal end of end section 474, to expand radially outward. As the burr begins spinning, centrifugal force expands the tube section. Fluid then fills the interior cavity of the tube section 480 through drive shaft 424 and is also acted on by the centrifugal force. To prevent the tube section 480 from over expanding, the tube section expands only at the channel-like sections 484 located between the ribs. As the channel-like sections 484 stretch and the tube section expands, the curvilinear ribs 482 begin to straighten. Once the ribs straighten, further expansion of the tube section 480 is inhibited. As the rotational speed of the ablation burr is decreased, the outer diameter of the burr decreases so that the burr can be withdrawn through the catheter.

In the preferred present embodiment, the expanding tube or sheath section 480 is made from a polymeric material such as polyurethane. However, other polymeric or elastomeric material may be used.

It will be appreciated to one of ordinary skill in the art that the dimensions of the curvilinear ribs can be chosen to determine the maximum expansion diameter of the burr so as to avoid rupturing the burr.

FIGS. 15A-15B illustrate another embodiment of an ablation burr according to the present invention. Referring to FIGS. 15A-15B, the expandable ablation burr 490 is mounted to the distal end of a conventional drive shaft 424 that rotates the burr at high speeds. Ablation burr 490 includes a tube section 500 with proximal and distal ends having an abrasive 510 disposed on at least a portion of the outside surface of the tube. The distal end of tube section 500 is attached to the stepped portion 496 of the nose section 492 and the proximal end of the tube is attached to the stepped portion 498 of end section 494 as previously described in connection with the embodiment shown in FIG. 9. As shown in FIG. 15A, tube section 500 includes two tubes 502, 504 of a polymeric material such as polyurethane or polyethylene. Braided layers of fiber 506, 508 are located in-between polymeric tubes 502, 504 to control the expansion of the burr.

Still referring to FIG. 15A, a polymeric material is extruded into small diameter tube 502. The inner tube 502 is placed onto a braiding machine (not shown) and a layer of fiber 506 is wrapped around the tube at an angle $\alpha$. A second layer of fiber 508 is wrapped around the first layer of fiber 506 at an angle $\theta$. Angle $\theta$ is usually the same angle as angle $\alpha$ of the first layer but in the opposite direction. The fibers of the second layer is oriented at an angle $\theta$ to with respect to the fibers of the first layer. A final outer tube 504 of polymeric material is extruded over the layered fibers to create a unified tube section 500. The abrasive 510 is disposed at the distal end of the outer surface of the tube section 500 and preferably comprises small diamond chips approximately 2-60 microns in size. Abrasive 510 is secured to the tube using an electro or electro-less plating method as described above. Other methods such as high-vacuum or pulse cathode arc ion deposition may also be used as earlier described.

As the drive shaft is rotated, the ablation burr is expanded due to centrifugal force. Prior to expansion, the layers of fibers are disposed with respect to each other at a predetermined angle $\beta$. As the tube section expands, the fiber layers follow the expansion of the tube section by moving toward a position that is transverse to the longitudinal axis of the burr. This movement causes angle $\theta$ and angle $\alpha$ to change. As soon as the angle $\beta$ reaches 47.2 degrees, or the neutral angle, the fiber layers stop moving or expanding with the tube section. The stoppage in the movement of the fiber layer restricts the outer diameter of the burr from expanding past this maximum diameter. A more detailed explanation of this can be found in U.S. Pat. No. 4,706,670, which is incorporated herein by reference. As the rotational speed of the ablation burr is decreased, the outer diameter of the burr decreases so that the burr can be withdrawn through the catheter.

It will be appreciated to one of ordinary skill in the art that multiple layers of fiber may be wound around the small diameter tube. It will also be appreciated that the fibers can be arranged at any pre-determined angle $\beta$ so that the desired ultimate expansion diameter can be achieved.

In the presently preferred embodiment of the invention, the fibers should be relatively non-elastic, but flexible and should have a suitable denier size in order to make a thin wall composite structure. An example of such a fiber is a liquid polymer crystal sold under the name Vectran®. However, other fibers having these characteristics may also be used.

With respect to the above discussed embodiments and any other potential embodiments, it may be desirable to etch or mask a portion of the tube so that the abrasive plating is laid in a pattern of dots or other shapes so that the abrasive layer does not completely surround the tube. If the abrasive is only plated to the etched pattern, it may allow the tube to more easily expand and collapse.

As can be seen from the above description, the present invention provides various mechanisms for controlling the maximum expanded diameter of an ablation burr. By controlling the expanded diameter of the burr, it is not necessary to remove the burr, drive shaft and catheter in order to ablate a larger diameter lumen in a patient.

In many instances, it is desirable to have an expandable ablation system that prevents the loose ablated particulate or gromous from embolizing into a distal vasculature. In Saphenous Vein Grafts (SVG) and In-stent Restenosis, the occluded material or gromous is friable, and conventional devices may break off large pieces of this material rather easily. This can cause the loose material or ablated particulate to flow downstream and embolize. To eliminate the need for multiple ablation burrs and to aid in the prevention of ablated particulate flowing downstream and embolizing, another aspect of the invention is a reverse pull-back ablation burr system that ablates the occlusion in a patient's vessel. The reverse pull-back ablation burr removes the occluding material from the vessel while reducing the possibility of the ablated particulate from embolizing.

FIGS. 16A-16C illustrate an embodiment of an ablation burr system according to the present invention that uses a reverse pull-back burr to ablate an occlusion. The atherectomy device 520 is routed from a position outside a patient's body to a point near the site of a SVG lesion through a guide catheter 522. Extending through the guide catheter 522 is an aspiration catheter or sheath 528 and a drive shaft that is coupled at its proximal end to a source of rotational motion such as an electric motor or gas turbine (not shown) that rotates the drive shaft 524 at high speeds, e.g., between 20,000 and 250,000 rpm. Disposed at the distal end of the drive shaft 524 is an ablation burr 530 that when rotated by the drive shaft 524 ablates a new lumen through the occlusion in order to permit blood to flow freely through the vessel 518. Extending through the drive shaft 524 and the ablation burr 530 is a guide wire 526 that can be steered by a physician in order to guide the ablation burr through the SVG occlusion.

Referring to the embodiment of the present invention as shown in FIGS. 16A-16C, the ablation burr 530 comprises a length of hypotube 532 coupled to a distal end of the drive shaft 524. The hypotube 532 includes one or more holes 534 that allow fluid to flow in or out of the hypotube 532. Surrounding the hypotube 532 is a polymeric balloon section 536 with proximal and distal ends, having an abrasive 538 disposed on at least a portion of the outer surface of the balloon. Referring to FIG. 16B, polymeric balloon section 536 is bonded at its proximate and distal ends to the hypotube 532.

As shown in FIGS. 16A-C, a smooth surface 540 of balloon section 536 begins at approximately the midpoint of balloon section 536 and extends to its distal end. Smooth side 540 helps to prevent the ablation burr 530 from scraping the vessel wall that may cause irritation and weaken the vessel. Abrasive 538 is attached to the proximal half end of balloon section 536 to remove the occluded material or gromous 542 when the ablation burr 530 is pulled back toward the guide catheter 522.

Balloon section 536 in an unexpended state (not shown) is furled or folded around the hypotube 532 so that ablation burr 530 has a minimal diameter that may be positioned through the occluded vessel. Balloon section 536 may be furled like convention percutaneous transluminal coronary angioplasty (PTCA) balloons as shown and described in U.S. Pat. No. 5,342,307, which is incorporated herein by reference. When the ablation burr 530 is in its furled condition and routed through the occlusion, abrasive 538 is partially covered by the smooth side 540 of the balloon section to prevent the breaking off of gromous 542. Alternatively, a sheathed balloon (not shown) or thin tube may be placed over the ballon section 536 to ease in the placement of the burr. The sheathed balloon covers the abrasive when routed to the distal end of the occlusion, and then may be pulled off when the burr is ready to expand.

Referring again to FIG. 16A, balloon section 536 in an expanded state will have a maximum outer diameter which is small enough not to dilate the SVG, but large enough to create a seal 544 and prevent ablated particulate from flowing past the ablation burr. The seal may have a boundary layer of fluid at the smooth side 540 of the balloon section 536 or may be coated with a hydrophilic coating such as Hydropass™. Alternatively, a distal ballon (not shown) or filter (not shown) could be deployed at the distal side of the burr so as to prevent ablated particulate from embolizing.

In operation, ablation burr 530 is routed through the SVG lesion on guide wire 526 in its furled state. Once past the lesion, ablation burr 530 is spun up to speed by drive shaft 524, which is rotated by rotational means such as a gas turbine or an electric motor. When the drive shaft 524 is rotated, fluid surrounding the drive shaft or within the drive shaft enters balloon section 536 through holes 534 in hypotube 532 to force the balloon to unfurl and expand to its maximum diameter to seal the vessel. Once the burr is rotated to its maximum speed and a seal 544 is created by the balloon section 536, the burr is pulled back through the lesion toward the guide catheter 522. As the burr passes through the lesion, abrasive 538 ablates the occluded material or gromous 542 and ablated particulate 546 is detached from the vessel wall. The seal 544 created by the balloon section 536 prevents this ablated particulate 546 from flowing downstream and possibly embolizing. Aspiration catheter 522 develops a slight vacuum with respect to blood pressure in the range of negative 25 to positive 120 mm of mercury to aspirate the ablated particulate 546 from the vessel 518. After the new lumen in formed in the vessel 518, the rotation of ablation burr 530 is reduced so that the burr may be withdrawn through guide catheter 522.

The balloon section 536 refurls back into its original, unexpanded state as soon as the ablation burr 530 ceases to rotate and the inflation fluid withdraws from the inner cavity of balloon section. The ability to refurl back into its original shape like conventional PTCA balloons is not the subject of the present invention. A more detailed description of a conventional PTCA balloon that can refurl back to its original shape is shown and described in U.S. Pat. No. 5,456,666, which is incorporated herein by reference.

In the presently preferred embodiment of the invention, balloon section 536 is made from a non-stretchable or non-compliant plastic material such as an oriented polyethylene terephthalate polymer (PET) or Mylar. However, other non-compliant polymeric or semi co-polymeric material may be used.

The abrasive 438 disposed at the proximal end of the outer surface of the balloon preferably comprises small diamond chips approximately 2-60 microns in size. Abrasive 438 is secured to the tube using an electro or electro-less plating method. This method has been previously described in the embodiment shown in FIG. 1. Other methods such as high-vacuum or pulse cathode arc ion deposition may also be used as earlier described. The abrasive may be plated in a triangular pattern on the proximal end between the folds of the balloon.

Alternatively, as shown in FIG. 16C, hypotube 532 may be constructed in two sections. Balloon section 536 is bonded to a distal hypotube section 548 and a proximal hypotube section 550. In this configuration, holes 534 are not required in the hypotube sections to allow fluid to enter the interior space of balloon section 536. Fluid enters through drive shaft 524, hypotube sections 548, 550 to expand balloon section 536.

FIGS. 17A-19C illustrate another embodiment of an ablation burr system according to the present invention that uses a reverse pull-back burr to ablate the occlusion. The ablation device is routed from a position outside a patient's body to a point near the site of a SVG lesion through a guide catheter (not shown). Extending through the guide catheter is an aspiration catheter or sheath 574 and a drive shaft 576 (FIGS. 19A, 19B) that is coupled at its proximal end to a source of rotational motion such as an electric motor or gas turbine (not shown) that rotates the drive shaft 576 at high speeds, e.g., between 20,000 and 250,000 rpm. Disposed at the distal end of the drive shaft 576 is an ablation burr 580 that when rotated by the drive shaft 576 ablates a new lumen through the lesion 566 in order to permit blood to flow freely through the vessel 568. Extending through the drive shaft 576 and the ablation burr 580 is a guide wire 578 that can be steered by a physician in order to guide the ablation burr through the SVG lesion.

Referring to FIGS. 18A-18C, the ablation burr 580 includes a torquable inner tube 582 coupled to a distal end of the drive shaft 576. The inner tube 582 includes one or more holes 584 that allow fluid to flow into or out of the inner tube 582. Surrounding the inner tube 582 is a balloon section 586 with proximal and distal ends 588, 590. A wire mesh 592 is disposed over the proximal end 588 of the balloon section and has an abrasive (not shown) disposed on at least a portion of its outer surface. Referring to FIGS. 18B and 18C, balloon section 586 is bonded at its proximal and distal ends to the inner tube 582.

The inner tube 582 includes an inflation lumen 596 that is coupled to a perfusion pump (not shown) that supplies saline or other fluid needed to inflate the balloon. The inflation lumen 596 extends through the inner tube 582 to accommodate guide wire 578. A distal seal 598 is disposed around the guide wire 578 at the distal end of inner tube 582 to create a closed, sealed inner tube so the perfusion system may operate to expand the balloon. The distal seal 598 is a conventional seal such as an o-ring or the like.

As shown in FIG. 18A, the proximal end 588 of balloon section 586 is bonded to the outer surface of the proximal end of inner tube 582. Drive shaft 576 surrounds and is coupled to the proximal end 588 of the balloon. An outer tube 600 is secured to the drive shaft 576 by welding, brazing or the like. Outer tube 600 is disposed around the drive shaft 576 and is concentric to inner tube 582. Outer tube 600 is preferably made out of PTFE to provide a lubricious surface when routing the ablation burr through the vasculature.

Figure 17A:
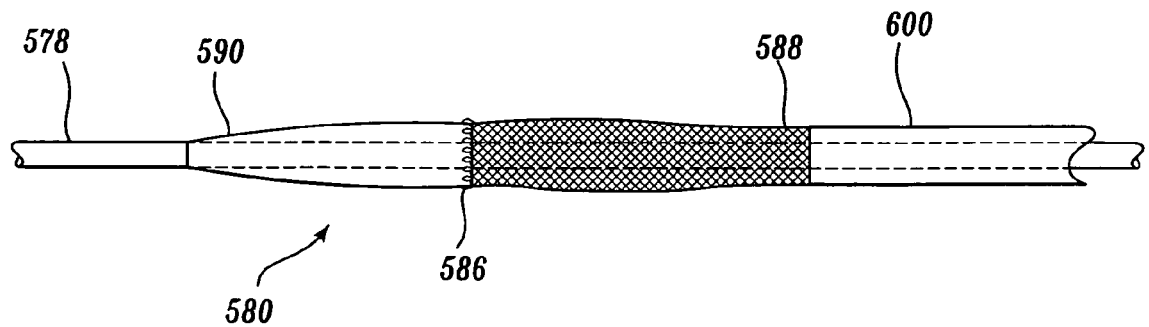
FIG. 17A illustrates another embodiment of the reverse pull-back expandable ablation burr system according to the present invention in its wrapped down state.
Figure 17B:
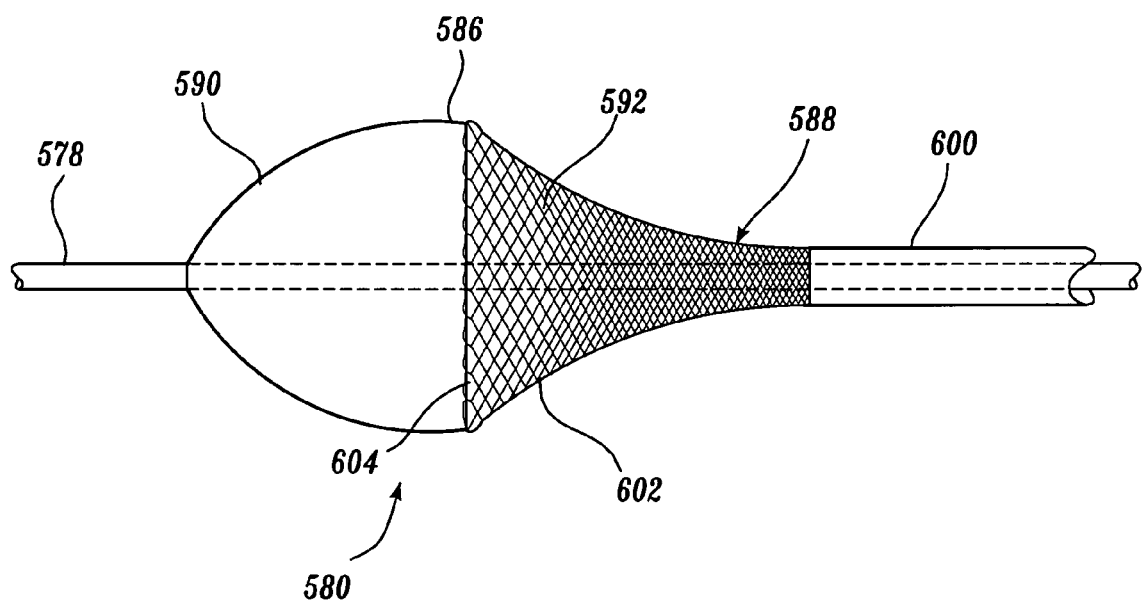
FIG. 17B illustrates the reverse pull-back expandable ablation burr system of FIG. 17A according to the present invention in its expanded state.
Figure 17C:
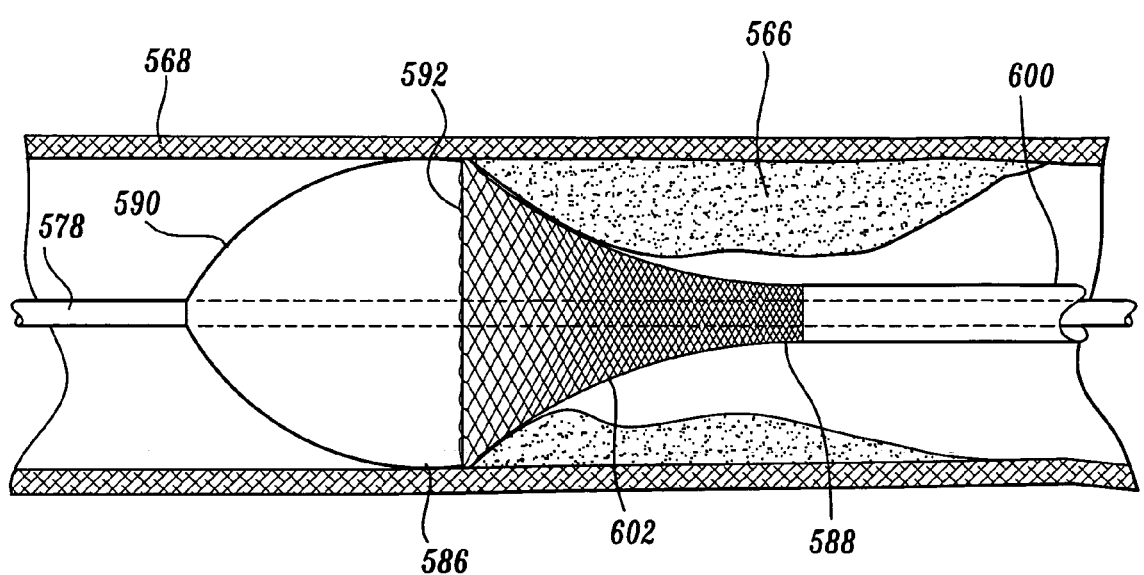
FIG. 17C illustrates the reverse pull-back expandable ablation burr system of FIG. 17A according to the present invention in its expanded state within an occluded vessel.

As shown in FIG. 17B, wire mesh 592 is coupled to the balloon 586 so that the proximal end 588 of the balloon forms a concave shaped section 602 when expanded. Wire mesh 592 begins at the proximal end 588 of the balloon and extends to approximately between the midpoint and the end of the balloon. In an actual embodiment, the wire mesh 592 extends from the proximal end of the balloon past the midpoint to approximately three quarters (¾) of the length of the balloon. The ends of wire mesh terminate with a loop 604 of additional or stored wire (FIG. 18A). The loop 604 allows for the wire mesh 592 to expand with the balloon while controlling the balloon's shaped. Wire mesh 592 is embedded into the balloon 586 so that the outer surface of the mesh is approximately flush with the outer surface of the balloon. Abrasive (not shown) is attached to the exposed wire mesh to remove the occluded material 566 when the ablation burr 580 is pulled back toward the guide catheter.

Also included in the ablation burr system is an aspiration catheter or sheath 574. Aspiration sheath 574 is routed through a guide catheter and coupled to an aspiration pump/filter system (not shown) at its proximal end. The aspiration pump creates a slight vacuum in the range of minus 10 mm of mercury to reverse the flow of the fluid and loose particulate 606 so that it may be removed from the vessel 566. Coupled to the inside surface of the aspiration sheath 574 is a self-expanding seal 608.

As seen in FIGS. 19C and 19D, the self expanding seal 608 includes a polymeric balloon 610 with a spring metal mesh 612 disposed within the balloon 610. Seal 608 has a maximum diameter slightly less than the vessel so that it blocks the blood flow through the vessel. Seal 608 is withdrawn or pulled into aspiration sheath 574 by a wire (not shown) and assumes a compressible state. Referring to FIGS. 19A and 19B, self expanding seal 608 is deployed by advancing the seal out through the distal end 575 of the aspiration catheter 574. Seal 608 self expands or springs out to resume its original maximum diameter due to the compression of the spring metal within the seal. In the presently preferred embodiment of the invention, the spring metal mesh 612 is made of a superelastic metal such as Nitinol™.

Alternatively, a guide catheter (not shown) may serve as both the guide catheter and the aspiration catheter. In this configuration, the self expanding seal would be coupled to and the aspiration pump/filter would be in fluid flow communication with the dual purpose guide catheter.

As shown in FIG. 17A, the ablation burr 580 is routed through the guide catheter and past the lesion in an unexpanded or wrapped down state. In the unexpanded state, the loops 604 of wire mesh 592 forms a forward cutting surface on the outside surface of the balloon at approximately the distal quarter (front ¼) of the burr. If the lumen is too occluded to route the burr past the lesion, the burr is rotated and the forward cutting surface ablates a passage through the lesion. The burr is rotated at a slower speed as compared to the rotational speed of the burr at its expanded state so as not to expand the burr.

In operation, as shown in FIG. 19A-19D, ablation burr 580 is routed through the lesion on guide wire 578 in its unexpanded or wrapped down state. If the lumen in the vessel 568 is not large enough because of the lesion 566, the ablation burr 580 is rotated at a lower speed to maintain a small diameter (i.e. 1.00-1.25 mm) to ablate a path as it passes through the lesion to the distal end. Because wire mesh 592 forms a forward cutting surface when the burr is in an unexpanded state, a large enough lumen is ablated to allow the burr to be routed past the lesion (FIG. 19B). Once past the lesion, the ablation burr 580 is spun up to speed by drive shaft 576 and perfusion is started by supplying saline to the inner tube 582. As the drive shaft 576 is rotated, fluid within the drive shaft enters balloon section 586 through holes 584 in inner tube 582 to force the balloon to expand. After perfusion has begun, the self expanding seal 608 is advanced and deployed at the proximal side of the lesion 566 as demonstrated in FIG. 19D. Once the seal is in place, the pressure at the ablation burr (distal pressure) is greater than the pressure behind the seal (proximal pressure). A minus 10 mm of mercury vacuum is created by the aspiration pump (not shown) and supplied to the aspiration sheath 574. The burr is expanded to a larger, first diameter (i.e. 2.00 mm) and pulled back toward the proximal side of the lesion. As the burr passes through the lesion, abrasive 594 ablates the occluded material and ablated particulate 606 is detached from the vessel wall. The detached, ablated particulate 606 is drawn into the aspiration catheter and removed from the vessel. The burr is again advanced forward through the lesion to the distal side and expanded to a larger, final diameter (i.e. 3.00 mm) for another pass back through the lesion 566. The burr is rotated at a lower speed (20,000 rpm) to cause a more aggressive cut. The aggressive cuts result in large ablated particulate 606 that must be removed through the aspiration sheath 574. A final pull back diameter is determined so there is complete removal of the lesion. The final pull back diameter is determined by expanding the burr at the distal side of the lesion until the perfusion pressure in the vasculature rises suddenly. Ultrasound may also be used for the final pull back diameter of the burr. The final pull back of the ablation burr 580 is performed slowly with careful monitoring of the distal pressure. After the new lumen in formed in the vessel 568, the rotation of ablation burr 580 decreases and the inflation fluid is withdrawn by the perfusion pump (not shown) so that the burr may be withdrawn through the guide catheter.

It will be appreciated by one of ordinary skill in the art that the burr was described in operation as making two passes through the occlusion at particular diameters. However, it may be desirable to make more or fewer passes through the lesion at different diameters as needed to completely remove the occluded material.

The abrasive (not shown) disposed at the proximal end 588 of the outer surface of the balloon preferably comprises small diamond chips approximately 2-60 microns in size. The abrasive is secured to the tube using an electro or electro-less plating method as described above. Other methods such as high-vacuum or pulse cathode arc ion deposition may also be used as earlier described.

In the presently preferred embodiment, the balloon 586 is made of a polymeric material such as a polyolefin copolymer. However, other polymeric materials may be used. Further, it may be desirable to use a porous polymer matrix balloon infuse with flushing fluid so that when the burr is rotated, the infused polymer matrix leaks fluid and flushes the ablated particulate into the aspiration sheath. Further, in the presently preferred embodiment, the wire mesh 592 is a metal material such as stainless steel. However, other materials such as polymers may be used.

In some instances, it may be desirable to coat the outer surface of the polymeric balloon with a hydrophilic coating such as Hydropass™, available from Boston Scientific and described in U.S. Pat. No. 5,702,754. The hydrophilic coating attracts water molecules, thereby making the surface slippery and easier to advance along the guide catheter. In addition, the hydrophilic coating may be beneficial during ablation since less torque may be transferred to a vessel wall if the burr stalls. In addition, the differential cutting ability of the burr may be enhanced due to the increased ability of the burr to slide over soft tissues.

It will be appreciated by one of ordinary skill in the art that the presently preferred embodiment may also be used in other surgical procedures such as percutaneous endarterectomy. Further, it will be appreciated that the ablation burr system may be used to ablate a new lumen through peripheral vasculatures or to remove occlusions from Restenosis Stents.

While the preferred embodiments of the invention has been illustrated and described, it will be appreciated that various changes can be made therein without departing from the spirit and scope of the invention. The scope of the invention should therefore be determined from the following claims and equivalents thereto.

The embodiments of the invention in which an exclusive property or privilege is claimed are defined as follows:

1. A device for ablating an occlusion in a patient's vasculature, comprising:
    a rotary drive shaft;
    a drive source operatively connected to the rotary drive shaft for rotating the rotary drive shaft; and
    an occlusion removal device secured to the rotary drive shaft for rotation therewith, the occlusion removal device comprising a polymeric balloon section, the polymeric balloon section being configured to expand in a controlled manner between a first cross-sectional area and a second larger predetermined maximum cross-sectional area, wherein a portion of the balloon includes an abrasive exterior surface.

2. The device of claim 1, wherein the polymeric balloon section includes means for controlling the expansion of the polymeric balloon section between the first cross-sectional area and the second larger cross-sectional area.

3. The device of claim 1, wherein after the second larger cross-sectional area is attained, the cross-sectional area of the balloon is independent of higher rotational speeds of the rotary drive shaft.

4. A device for ablating an occlusion in a patient's vasculature, comprising:
    a rotary drive shaft;
    a drive source operatively connected to the rotary drive shaft for rotating the rotary drive shaft; and
    an occlusion removal device secured to the rotary drive shaft for rotation therewith, the occlusion removal device comprising a polymeric balloon section, the polymeric balloon section being expandable in a controlled manner between a first diameter and a second larger diameter upon rotation of the occlusion removal device, wherein a portion of the balloon includes an abrasive exterior surface.

5. The device of claim 4, wherein the polymeric balloon section is an elastomeric balloon section.

6. The device of claim 4, wherein the occlusion removal device includes means for controlling the expansion of the polymeric balloon section between the first diameter and the second larger diameter.

7. The device of claim 6, wherein the polymeric balloon section includes the means for controlling the expansion of the polymeric balloon sections.

8. A medical device, comprising:
    a rotary drive shaft;
    a drive source that rotates the rotary drive shaft at a selected speed measured in revolutions per minute; and an occlusion removal device secured to the rotary drive shaft for rotation therewith, the occlusion removal device comprising a polymeric balloon section, the polymeric balloon section being expandable in a controlled manner between a first cross-sectional area and a second larger cross-sectional area, wherein a portion of the balloon includes an abrasive exterior surface.

9. The medical device of claim 8, further comprising means for controlling the expansion of the polymeric balloon section between the first cross-sectional area and the second larger cross-sectional area.

10. The device of claim 9, wherein the occlusion removal device includes the means for controlling the expansion of the polymeric balloon section.

* * * * *